United States Patent
Madiyalakan et al.

(10) Patent No.: US 10,392,444 B2
(45) Date of Patent: Aug. 27, 2019

(54) TUMOR ANTIGEN SPECIFIC ANTIBODIES AND TLR3 STIMULATION TO ENHANCE THE PERFORMANCE OF CHECKPOINT INTERFERENCE THERAPY OF CANCER

(71) Applicant: ONCOQUEST INC., Edmonton, Alberta (CA)

(72) Inventors: Ragupathy Madiyalakan, Edmonton (CA); Christopher F Nicodemus, Charlestown, MA (US)

(73) Assignee: Oncoquest, Inc., Edmonton, Alberta (CA)

( * ) Notice: Subject to any disclaimer, the term of this patent is extended or adjusted under 35 U.S.C. 154(b) by 0 days.

(21) Appl. No.: 15/501,773

(22) PCT Filed: Aug. 7, 2015

(86) PCT No.: PCT/CA2015/050747
§ 371 (c)(1),
(2) Date: Feb. 3, 2017

(87) PCT Pub. No.: WO2016/019472
PCT Pub. Date: Feb. 11, 2016

(65) Prior Publication Data
US 2017/0226221 A1    Aug. 10, 2017

Related U.S. Application Data

(60) Provisional application No. 62/034,915, filed on Aug. 8, 2014.

(51) Int. Cl.
| | |
|---|---|
| C07K 16/28 | (2006.01) |
| C07K 16/30 | (2006.01) |
| A61K 39/395 | (2006.01) |
| A61K 31/713 | (2006.01) |
| A61K 39/39 | (2006.01) |
| C07K 16/10 | (2006.01) |
| A61K 39/00 | (2006.01) |

(52) U.S. Cl.
CPC ........ *C07K 16/3092* (2013.01); *A61K 31/713* (2013.01); *A61K 39/39* (2013.01); *A61K 39/39558* (2013.01); *C07K 16/1063* (2013.01); *C07K 16/2827* (2013.01); *C07K 16/303* (2013.01); *A61K 2039/507* (2013.01); *A61K 2039/55561* (2013.01); *C07K 2317/21* (2013.01); *C07K 2317/30* (2013.01); *C07K 2317/34* (2013.01); *C07K 2317/56* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | | |
|---|---|---|---|---|
| 2002/0132771 | A1* | 9/2002 | Madiyalakan | A61K 41/0057 424/131.1 |
| 2004/0191168 | A1* | 9/2004 | Dent | A61K 31/52 424/1.49 |
| 2009/0055944 | A1* | 2/2009 | Korman | C07K 16/28 800/18 |
| 2010/0266617 | A1* | 10/2010 | Carven | C07K 16/2818 424/172.1 |

FOREIGN PATENT DOCUMENTS

| | | |
|---|---|---|
| WO | 2008091643 A2 | 7/2008 |
| WO | 2013/063312 A1 | 2/2013 |

OTHER PUBLICATIONS

'Mac' Cheever, Immunol. Rev., 2008, 222:357-368.*
International Search Report in PCT/CA2015/050747, dated Nov. 4, 2015.
Andre et al., "Molecular Pathways: Involvement of immune Pathways in the Therapeutic Response and Outcome in Breast Cancer," Clin. Cancer. Res., Jan. 2013, vol. 19, pp. 28-33.
Bhardwaj, et al., "TLR Antagonists: Are They Good Adjuvants?," Cancer J., Jul. 2010, vol. 16, pp. 382-391.
Stagg, et al., "Anti-ErbB-2 mAb Therapy Requires Type I and II Interferons and Synergizes with AAnti-PD-1 or Anti-CD137 mAb Therapy," PNAS USA, Apr. 2011, vol. 108, pp. 7142-7147.
Tse, et al., "Antibody-Based Immunotherapy for Ovarian Cancer: Where are we at?," Annals of Oncology, Feb. 2014, vol. 25, pp. 322-331.
Wang et al., "In Vitro Characterization of the Anti-PD-1 Antibody Nivolumab, PMS-936558, and in vivo toxicology in Non-Human Primates," Cancer Immunol. Res., Online May 2014, vol. 2, pp. 846-856.
Toshihiro et al.: "A novel combinatorial cancer immunotherapy: poly-IC and blockade of the PD-1/PD-L1 pathway", OncoImmunology, vol. 3, May 2014, pp. e28440-1-e28440-3.
Mehla et al.: "Combination of mAb-AR20.5, anti-PD-L1 and PolyICLC inhibits tumor progression and prolongs survival of MUC1.Tg mice challenged with pancreatic tumors", Cancer Immunology, Immunotherapy, Dec. 2017.
Teo et al.: "Using the allergic immune system to target cancer: activity of IgE antibodies specific for human CD20 and MUC1", Cancer Immunology, Immunotherapy, vol. 61, Jun. 2012, pp. 2295-2309.

(Continued)

*Primary Examiner* — Hong Sang
(74) *Attorney, Agent, or Firm* — Kilpatrick Townsend & Stockton LLP

(57) ABSTRACT

The present disclosure relates to a method for inhibiting cancer tumor growth in a patient by administering to the patient a therapeutic monoclonal antibody specific for a tumor associated antigen in combination with at least one immunostimulatory compound, and at least one immune homeostatic checkpoint inhibitor. Also disclosed are uses, compositions and kits thereof.

9 Claims, 14 Drawing Sheets

Specification includes a Sequence Listing.

(56) References Cited

OTHER PUBLICATIONS

Cascio et al. "MUC1 Protein Expression in Tumor Cells Regulates Transcription of Proinflammatory Cytokines by Forming a Complex with Nuclear Factor-kB p65 and Binding to Cytokine Promoters: Importance of Extracellular Domain", The Journal of Biological Chemistry, vol. 286, Dec. 2011, pp. 42248-42256.

Supplementary European Search Report of 15829910.7, The Hague, dated Jan. 8, 2018, Stitch, David.

Möbus, et al. "Immune responses to murine monoclonal antibody-B43.13 correlate with prolonged survival of women with recurrent ovarian cancer." American journal of obstetrics and gynecology 189, No. 1 (2003): 28-36.

Nagato, et al. "Combinatorial immunotherapy of polyinosinic-polycytidylic acid and blockade of programmed death-ligand 1 induce effective CD8 T-cell responses against established tumors." Clinical Cancer Research 20, No. 5 (2014): 1223-1234.

Naidoo, et al. "Immune checkpoint blockade." Hematology/Oncology Clinics 28, No. 3 (2014): 585-600.

Pauken, et al. "Epigenetic stability of exhausted T cells limits durability of reinvigoration by PD-1 blockade." Science 354, No. 6316 (2016): 1160-1165.

Qi, et al. "Characterization of an anti-MUC1 monoclonal antibody with potential as a cancer vaccine." Hybridoma and hybridomics 20, No. 5-6 (2001): 313-324.

Teo, et al. "Using the allergic immune system to target cancer: activity of IgE antibodies specific for human CD20 and MUC1." Cancer Immunology, Immunotherapy 61, No. 12 (2012): 2295-2309.

\* cited by examiner

SEQUENCE LISTING

<160> NUMBER OF SEQ ID NOS: 5

<210> SEQ ID NO 1
<211> LENGTH: 428
<212> TYPE: DNA
<213> ORGANISM: Artificial Sequence
<220> FEATURE:
<223> OTHER INFORMATION: Synthetic polynucleotide
<220> FEATURE:
<223> OTHER INFORMATION: 3C6.hIgE heavy chain variable:

<400> SEQUENCE: 1

```
gccgccacca tgtacttggg actgaactgt gtattcatag tttttctctt aaatggtgtc      60
cagagtgaag tgaagcttga ggagtctgga ggaggcttgg tgcaacctgg aggatccatg     120
aaactctctt gtgctgcctc tggattcact tttagtgacg cctggatgga ctgggtccgc     180
cagtctccag agaaggggct tgagtgggtt gctgaaatta agcaaagc taataatcat     240 gcaacatact atgctgagtc tgtgaaaggg aggttcacca tctcaagaga tgtttccaaa     300
agtagtgtct acctgcaaat gaacaactta agagctgaag acactggcat ttattactgt     360
accagggggg ggtacggctt tgactactgg ggccaaggca ccactctcac agtctcctca     420
ggtaagtg                                                               428
```

<210> SEQ ID NO 2
<211> LENGTH: 409
<212> TYPE: DNA
<213> ORGANISM: Artificial Sequence
<220> FEATURE:

<223> OTHER INFORMATION: Synthetic polynucleotide
<220> FEATURE:
<223> OTHER INFORMATION: 3C6.hIgE light chain variable

<400> SEQUENCE: 2

```
gccgccacca tgaagttgcc tgttaggctg ttggtgctga tgttctggat tcctgcttcc      60
agcagtgatg ttttgatgac ccaaactcca ctctccctgc ctgtcagtct ggagatcaa     120
gcctccatct cttgcagatc tagtcagagc attgtacata gtaatggaaa cacctattta    180
gaatggtacc tgcagaaacc aggccagtct ccaaagctcc tgatctacaa agtttccaac    240
cgattttctg gggtcccaga caggttcagt ggcagtggat cagggacaga tttcacactc    300
aagatcagca gagtggaggc tgaggatctg ggagtttatt actgctttca aggttcacat    360
gttccgctca cgttcggtgc tgggaccaag ctggagctga aacgtaagt                409
```

<210> SEQ ID NO 3
<211> LENGTH: 427
<212> TYPE: DNA
<213> ORGANISM: Artificial Sequence
<220> FEATURE:
<223> OTHER INFORMATION: Synthetic polynucleotide
<220> FEATURE:
<223> OTHER INFORMATION: 4H5.hIgE monoclonal antibody heavy chain variable region

<400> SEQUENCE: 3

```
gccgccacca tgggatggag ctgtatcatg ctcttttttgg tagcaacagc aacaggtgtc     60
cactcccagg tccaactgca gcagtctggg gctgaactgg tgaagcctgg ggcttcagtg    120
aagttgtcct gcaaggcttc tggctacacc ttcaccagct actatatgta ctgggtgaag    180
cagaggcctg acaaggcct tgagtggatt ggagagatta atcctagcaa tggtggtact    240
gacttcaatg agaagttcaa gagcaaggcc acactgactg tagacaaatc ctccagcaca    300
gcatacatgc aactcagcag cctgacatct gcggactctg cggtctatta ctgtacaagg    360
gggggtgatt acccctggtt tgcttactgg ggccaaggga ctctggtcac tgtctctgca    420
ggtaagt                                                               427
```

<210> SEQ ID NO 4
<211> LENGTH: 415
<212> TYPE: DNA
<213> ORGANISM: Artificial Sequence
<220> FEATURE:
<223> OTHER INFORMATION: Synthetic polynucleotide
<220> FEATURE:
<223> OTHER INFORMATION: 4H5.hIgE monoclonal antibody heavy chain variable region

<400> SEQUENCE: 4

```
gccgccacca tggattcaca ggcccaggtt cttatgttac tgctgctatg ggtatctggt     60
acctgtgggg acattgtgat gtcacagtct ccatcctccc tagctgtgtc agttggagag    120
aaggttacta tgagctgcaa gtccagtcag agccttttat atagtagcaa tcaaaagaac    180
tacttggcct ggtaccagca gaaaccaggg cagtctccta aactgctgat ttactgggca    240
tccactaggg aatctggggt ccctgatcgc ttcacaggca gtggatctgg gacagatttc    300
actctcacca tcagcagtgt gaaggctgaa gacctggcag tttattactg tcagcaatat    360
tatagctatc ctctcacgtt cggtgctggg accaagctgg agctgaaacg taagt         415
```

<210> SEQ ID NO 5
<211> LENGTH: 20

```
<212> TYPE: PRT
<213> ORGANISM: Homo sapiens
<220> FEATURE:
<223> OTHER INFORMATION: Amino Acid Sequence of MUC1 epitope

<400> SEQUENCE: 5

Ser Thr Ala Pro Pro Ala His Gly Val Thr Ser Ala Pro Asp Thr Arg
1               5                   10                  15

Pro Ala Pro Gly
            20
```

TUMOR ANTIGEN SPECIFIC ANTIBODIES AND TLR3 STIMULATION TO ENHANCE THE PERFORMANCE OF CHECKPOINT INTERFERENCE THERAPY OF CANCER

CROSS-REFERENCE TO RELATED APPLICATIONS

This application is a U.S. National Phase of PCT/CA2015/050747, filed Aug. 7, 2015, which claims the benefit of U.S. provisional patent application 62/034915, filed on Aug. 8, 2014, each of which is hereby incorporated by reference.

BACKGROUND (a) Field

The subject matter disclosed generally relates to methods for inhibiting cancer tumor growth in a patient. More specifically, the method relates to methods comprising administering to a patient a therapeutic monoclonal antibody specific for a tumor associated antigen in combination with at least one immunostimulatory compound, and at least one immune homeostatic checkpoint inhibitor.

(b) Related Prior Art

Quest PharmaTech has developed a series of monoclonal antibodies specific to tumor antigens such as CA125, MUC1, PSA, Her2/neu and other tumor associated antigens. Quest PharmaTech is developing these monoclonal antibody therapies as cancer immunotherapy specifically capable of stimulating anti-tumor immunity through altered antigen processing and presentation stimulated by these specific antibodies.

Demonstrations studies have been completed in animals and for several antibodies, namely AR20.5 and B43.13, in human clinical trials. Parallel to these efforts, immunologists studying the molecular events of adaptive immunity have defined the pathways of antigen recognition by specific T cells using T cell receptors that recognize peptide fragments of antigen in the context of MHC class I and II. The dynamics of an acute response require activation of second signals in addition to T cell receptor recognition to avoid induction of tolerance. The primary activating second signals are the interaction between B7.1 on antigen presenting cells (APC) and CD28 on the T cells. These second signals are induced in the pro-inflammatory microenvironment. Additional activating pathways have also been defined, as well as a redundant set of checkpoint pathways designed to limit antigen specific activation. These homeostatic checkpoint signals include the interaction of CTLA4 on T cells with B7.1 on APC and PD-1 on T cells with B7H1 on APC.

Interference with checkpoint inhibition results in prolongation and enhancement of specific immunity. This has been applied to the immunotherapy of multiple cancer types and as reported at the 2014 meeting of the American Society of Clinical Oncology, activation of immunity using molecules in development, as well as commercialized molecules in the case of one anti-CTLA-4 monoclonal antibody (ipilimumab), can result in predictable clinical responses, and durable control of tumor growth and, on occasion, shrinkage and elimination of disease in patients with advanced solid malignancy. Responses to therapy have been associated with the presence of mutations on common tumor antigens presumably creating Neoantigens that are more prone to immune attacks by endogenous T cells (Snyder et al ASCO Proceedings 2014 abstract 3003). The performance of immune checkpoint blockade therapies, however, remains limited, with responses seen in less than 50% of patents and complete responses observed in only a few percent of treated patients.

Therefore, there is a need for method that will improve the performance of immune checkpoint blockade therapies.

SUMMARY

According to an embodiment, there is provided a method for inhibiting cancer tumor growth in a patient comprising administering to the patient a therapeutic monoclonal antibody specific for a tumor associated antigen in combination with at least one immunostimulatory compound, and at least one immune homeostatic checkpoint inhibitor.

The tumor-associated target antigen may be expressed on the surface of a cell of the tumor.

The tumor-associated target antigen may be a soluble antigen.

The therapeutic monoclonal antibody specific for a tumor associated antigen may be an IgG antibody, an IgE antibody, or a combination thereof.

The therapeutic monoclonal antibody specific for a tumor associated antigen may be an antibody specific to MUC1.

The antibody specific to MUC1 binds an epitope of MUC1 selected from SEQ ID NO: 5.

The heavy chain variable region of the antibody specific to MUC1 may be encoded by a nucleic acid comprising SEQ ID NO: 1 and wherein a light chain variable region of the antibody specific to MUC1 may be encoded by a nucleic acid comprising SEQ ID NO: 2.

The heavy chain variable region of the antibody specific to MUC1 may be encoded by a nucleic acid comprising SEQ ID NO: 3 and a light chain variable region of the antibody specific to MUC1 may be encoded by a nucleic acid comprising SEQ ID NO: 4.

The antibody specific to MUC1 may be mAb-AR20.5, mAb 3C6.hIgE, mAb 4H5.hIgE or a combination thereof.

The therapeutic monoclonal antibody specific for a tumor associated antigen may be an antibody specific to CA125.

The antibody specific to CA125 may be mAb-B43.13.

The immunostimulatory compound may be a TLR3 agonist or a TLR4 agonist.

The TLR3 agonist may be polyIC, polyICLC (Hiltonol®).

The immune homeostatic checkpoint inhibitor an anti-PD-1 antibody, an anti-PDL-1, an anti-CTLA-4 antibody, or molecular inhibitors of these receptors.

The anti-PD-1 antibody may be selected from the group consisting of nivolumab antibody, pembrolizumab antibody, pidilizumab antibody or combinations thereof.

The anti-PDL-1 antibody may be selected from the group consisting of B7-H1 antibody, BMS-936559 antibody, MPDL3280A (atezolizumab) antibody, MEDI-4736 antibody, MSB0010718C antibody or combinations thereof.

The anti-CTLA-4 antibody may be selected from the group consisting of ipilimumab or tremelimumab or combinations thereof.

The therapeutic tumor associated antigen specific antibody may be murine monoclonal antibody (xenotypic), a chimeric monoclonal antibody, a humanized monoclonal antibody or a fully human monoclonal antibody.

The therapeutic monoclonal antibody specific for a tumor associated antigen may have a constant region that may be of human origin.

The therapeutic monoclonal antibody specific for a tumor associated antigen may have variable regions that are of human origin, non-human origin or any combination thereof.

The cancer may be selected from pancreatic cancer, breast cancer, colorectal cancer, ovarian cancer, renal cancer, prostate cancer, bladder cancer, gastrointestinal cancer, lung cancer and multiple myeloma.

The tumor associated antigen may be CA125, folate binding protein (FBP), HER2/neu, MUC1 or PSA.

The method mat comprise the steps of:
a) administering a therapeutically effective amount of the therapeutic monoclonal antibody specific for a tumor associated antigen;
b) administering a therapeutically effective amount of the immunostimulatory compound after step a); and
c) administering a therapeutically effective amount of the immune homeostatic checkpoint inhibitor, after step b).

The step b) may be performed 1 or more days after step a).

The step c) may be performed 1 or more days after step b).

According to another embodiment, there is provided a use of a therapeutic monoclonal antibody specific for a tumor associated antigen in combination with at least one immunostimulatory compound, and at least one immune homeostatic checkpoint inhibitor for inhibiting cancer tumor growth in a patient in need thereof.

The tumor-associated target antigen may be expressed on the surface of a cell of the tumor.

The tumor-associated target antigen may be a soluble antigen.

The therapeutic monoclonal antibody specific for a tumor associated antigen may be an IgG antibody, an IgE antibody, or a combination thereof.

The therapeutic monoclonal antibody specific for a tumor associated antigen may be an antibody specific to MUC1.

The antibody specific to MUC1 binds an epitope of MUC1 selected from SEQ ID NO: 5.

The heavy chain variable region of the antibody specific to MUC1 may be encoded by a nucleic acid comprising SEQ ID NO: 1 and wherein a light chain variable region of the antibody specific to MUC1 may be encoded by a nucleic acid comprising SEQ ID NO: 2.

The heavy chain variable region of the antibody specific to MUC1 may be encoded by a nucleic acid comprising SEQ ID NO: 3 and a light chain variable region of the antibody specific to MUC1 may be encoded by a nucleic acid comprising SEQ ID NO: 4.

The antibody specific to MUC1 may be mAb-AR20.5, mAb 3C6.hIgE, mAb 4H5.hIgE or a combination thereof.

The therapeutic monoclonal antibody specific for a tumor associated antigen may be an antibody specific to CA125.

The antibody specific to CA125 may be mAb-B43.13.

The immunostimulatory compound may be a TLR3 agonist or a TLR4 agonist.

The TLR3 agonist may be polyIC, polyICLC (Hiltonol®).

The immune homeostatic checkpoint inhibitor an anti-PD-1 antibody, an anti-PDL-1, an anti-CTLA-4 antibody, or molecular inhibitors of these receptors.

The anti-PD-1 antibody may be selected from the group consisting of nivolumab antibody, pembrolizumab antibody, pidilizumab antibody or combinations thereof.

The anti-PDL-1 antibody may be selected from the group consisting of B7-H1 antibody, BMS-936559 antibody, MPDL3280A (atezolizumab) antibody, MEDI-4736 antibody, MSB0010718C antibody or combinations thereof.

The anti-CTLA-4 antibody may be selected from the group consisting of ipilimumab or tremelimumab or combinations thereof.

The therapeutic tumor associated antigen specific antibody may be murine monoclonal antibody (xenotypic), a chimeric monoclonal antibody, a humanized monoclonal antibody or a fully human monoclonal antibody.

The therapeutic monoclonal antibody specific for a tumor associated antigen may have a constant region that may be of human origin.

The therapeutic monoclonal antibody specific for a tumor associated antigen may have variable regions that are of human origin, non-human origin or any combination thereof.

The cancer may be selected from pancreatic cancer, breast cancer, colorectal cancer, ovarian cancer, renal cancer, prostate cancer, bladder cancer, gastrointestinal cancer, lung cancer and multiple myeloma.

The tumor associated antigen may be CA125, folate binding protein (FBP), HER2/neu, MUC1 or PSA.

The therapeutic monoclonal antibody specific for a tumor associated antigen may be used prior to the immunostimulatory compound.

The immunostimulatory compound may be used prior to the immune homeostatic checkpoint inhibitor.

The monoclonal antibody specific for a tumor associated antigen may be used 1 or more days prior to the immunostimulatory compound.

The immunostimulatory compound may be used 1 or more days prior to the immune homeostatic checkpoint inhibitor.

According to another embodiment, there is provided a composition for use in inhibiting cancer tumor growth in a patient in need thereof, the composition comprising a therapeutic monoclonal antibody specific for a tumor associated antigen, at least one immunostimulatory compound, and at least one immune homeostatic checkpoint inhibitor.

The tumor-associated target antigen may be expressed on the surface of a cell of the tumor.

The tumor-associated target antigen may be a soluble antigen.

The therapeutic monoclonal antibody specific for a tumor associated antigen may be an IgG antibody, an IgE antibody, or a combination thereof.

The therapeutic monoclonal antibody specific for a tumor associated antigen may be an antibody specific to MUC1.

The antibody specific to MUC1 binds an epitope of MUC1 selected from SEQ ID NO: 5.

The heavy chain variable region of the antibody specific to MUC1 may be encoded by a nucleic acid comprising SEQ ID NO: 1 and wherein a light chain variable region of the antibody specific to MUC1 may be encoded by a nucleic acid comprising SEQ ID NO: 2.

The heavy chain variable region of the antibody specific to MUC1 may be encoded by a nucleic acid comprising SEQ ID NO: 3 and a light chain variable region of the antibody specific to MUC1 may be encoded by a nucleic acid comprising SEQ ID NO: 4.

The antibody specific to MUC1 may be mAb-AR20.5, mAb 3C6.hIgE, mAb 4H5.hIgE or a combination thereof.

The therapeutic monoclonal antibody specific for a tumor associated antigen may be an antibody specific to CA125.

The antibody specific to CA125 may be mAb-B43.13.

The immunostimulatory compound may be a TLR3 agonist or a TLR4 agonist.

The TLR3 agonist may be polyIC, polyICLC (Hiltonol®).

The immune homeostatic checkpoint inhibitor an anti-PD-1 antibody, an anti-PDL-1, an anti-CTLA-4 antibody, or molecular inhibitors of these receptors.

The anti-PD-1 antibody may be selected from the group consisting of nivolumab antibody, pembrolizumab antibody, pidilizumab antibody or combinations thereof.

The anti-PDL-1 antibody may be selected from the group consisting of B7-H1 antibody, BMS-936559 antibody, MPDL3280A (atezolizumab) antibody, MEDI-4736 antibody, MSB0010718C antibody or combinations thereof.

The anti-CTLA-4 antibody may be selected from the group consisting of ipilimumab or tremelimumab or combinations thereof.

The therapeutic tumor associated antigen specific antibody may be murine monoclonal antibody (xenotypic), a chimeric monoclonal antibody, a humanized monoclonal antibody or a fully human monoclonal antibody.

The therapeutic monoclonal antibody specific for a tumor associated antigen may have a constant region that may be of human origin.

The therapeutic monoclonal antibody specific for a tumor associated antigen may have variable regions that are of human origin, non-human origin or any combination thereof.

The cancer may be selected from pancreatic cancer, breast cancer, colorectal cancer, ovarian cancer, renal cancer, prostate cancer, bladder cancer, gastrointestinal cancer, lung cancer and multiple myeloma.

The tumor associated antigen may be CA125, folate binding protein (FBP), HER2/neu, MUC1 or PSA.

According to another embodiment, there is provided a kit for use in inhibiting cancer tumor growth in a patient in need thereof, the kit comprising a therapeutic monoclonal antibody specific for a tumor associated antigen, at least one immunostimulatory compound, at least one immune homeostatic checkpoint inhibitor, and instructions on how to use the kit.

The tumor-associated target antigen may be expressed on the surface of a cell of the tumor.

The tumor-associated target antigen may be a soluble antigen.

The therapeutic monoclonal antibody specific for a tumor associated antigen may be an IgG antibody, an IgE antibody, or a combination thereof.

The therapeutic monoclonal antibody specific for a tumor associated antigen may be an antibody specific to MUC1.

The antibody specific to MUC1 binds an epitope of MUC1 selected from SEQ ID NO: 5.

The heavy chain variable region of the antibody specific to MUC1 may be encoded by a nucleic acid comprising SEQ ID NO: 1 and wherein a light chain variable region of the antibody specific to MUC1 may be encoded by a nucleic acid comprising SEQ ID NO: 2.

The heavy chain variable region of the antibody specific to MUC1 may be encoded by a nucleic acid comprising SEQ ID NO: 3 and a light chain variable region of the antibody specific to MUC1 may be encoded by a nucleic acid comprising SEQ ID NO: 4.

The antibody specific to MUC1 may be mAb-AR20.5, mAb 3C6.hIgE, mAb 4H5.hIgE or a combination thereof.

The therapeutic monoclonal antibody specific for a tumor associated antigen may be an antibody specific to CA125.

The antibody specific to CA125 may be mAb-B43.13.

The immunostimulatory compound may be a TLR3 agonist or a TLR4 agonist.

The TLR3 agonist may be polyIC, polyICLC (Hiltonol®).

The immune homeostatic checkpoint inhibitor an anti-PD-1 antibody, an anti-PDL-1, an anti-CTLA-4 antibody, or molecular inhibitors of these receptors.

The anti-PD-1 antibody may be selected from the group consisting of nivolumab antibody, pembrolizumab antibody, pidilizumab antibody or combinations thereof.

The anti-PDL-1 antibody may be selected from the group consisting of B7-H1 antibody, BMS-936559 antibody, MPDL3280A (atezolizumab) antibody, MEDI-4736 antibody, MSB0010718C antibody or combinations thereof.

The anti-CTLA-4 antibody may be selected from the group consisting of ipilimumab or tremelimumab or combinations thereof.

The therapeutic tumor associated antigen specific antibody may be murine monoclonal antibody (xenotypic), a chimeric monoclonal antibody, a humanized monoclonal antibody or a fully human monoclonal antibody.

The therapeutic monoclonal antibody specific for a tumor associated antigen may have a constant region that may be of human origin.

The therapeutic monoclonal antibody specific for a tumor associated antigen may have variable regions that are of human origin, non-human origin or any combination thereof.

The cancer may be selected from pancreatic cancer, breast cancer, colorectal cancer, ovarian cancer, renal cancer, prostate cancer, bladder cancer, gastrointestinal cancer, lung cancer and multiple myeloma.

The tumor associated antigen may be CA125, folate binding protein (FBP), HER2/neu, MUC1 or PSA.

The following terms are defined below.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition or other compositions in general, is intended to encompass a product comprising the active ingredient(s) and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions or other compositions in general of the present invention encompass any composition made by admixing a compound of the present invention and a pharmaceutically acceptable carrier. By "pharmaceutically acceptable" or "acceptable" it is meant the carrier, diluent or excipient must be compatible with the other ingredients of the formulation and not deleterious to the recipient thereof.

In some embodiments, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the antibody or fragment thereof, preferably in purified form, together with a suitable amount of carrier so as to provide the form for proper administration to the patient. The formulation should suit the mode of administration.

The terms "inhibit", "inhibition" or "inhibiting" as used herein in the context of the invention means to slow, hinder, restrain reduce or prevent. For example, "inhibiting growth" of a tumor cell as that term is used herein means to slow, hinder, restrain, reduce or prevent the tumor cell from growing.

The term "administering" as used herein refers to any action that results in exposing or contacting a composition containing a therapeutic monoclonal antibody specific for a tumor associated antigen in combination with at least one immunostimulatory compound, and at least one immune homeostatic checkpoint inhibitor, according to the invention with a pre-determined cell, cells, or tissue, typically mammalian. As used herein, administering may be conducted in vivo, in vitro, or ex vivo. For example, a composition may be administered by injection or through an endoscope. Administering also includes the direct application to cells of a composition according to the present invention. For example, during the course of surgery, tumor cells may be exposed. In accordance with an embodiment of the invention, these exposed cells (or tumors) may be exposed directly to a composition of the present invention, e.g., by washing or irrigating the surgical site and/or the cells, or by direct intra-tumoral injection of the therapeutic monoclonal antibody specific for a tumor associated antigen in combination with at least one immunostimulatory compound, and at least one immune homeostatic checkpoint inhibitor individually or in a mixture.

The term "epitope" is intended to mean the portion of an antigen capable of being recognized by and bound by an antibody at one or more of the antibody's binding regions. Epitopes generally comprise chemically active surface groupings of molecules such as amino acids or sugar side chains and have specific three dimensional structure characteristics as well as specific charge characteristics. In one embodiment, an epitope of an antigen is a repetitive epitope. In one embodiment an epitope of an antigen is a non-repetitive epitope.

The term "subject" as used herein, is a human patient or other animal such as another mammal with functional mast cells, basophils, neutrophils, eosinophils, monocytes, macrophages, dendritic cells, and Langerhans cells. In humans, the appropriate cells express the high affinity receptor for IgG for the administered IgG antibody of the invention, as well as IgE (FcεRI) for the administered IgE antibody of the invention.

As used herein, a reduction in growth kinetics, or complete elimination of, a cancer tumor or a metastasized cell or tumor as used herein is defined to mean that which is as understood in the art. For example, a reduction in growth kinetics means a reduction in the exponential growth, specific growth rate, or doubling time of a primary solid tumor, metastasized cell, or metastasized tumor relative to the exponential growth, specific growth rate, or doubling time normally observed in vivo or in vitro for a given tumor type. Complete elimination of a tumor is the absence of tumor presence, either by symptoms, physical exam, or radiographic imaging, in the presence of the therapeutic monoclonal antibody specific for a tumor associated antigen in combination with at least one immunostimulatory compound, and at least one immune homeostatic checkpoint inhibitor, where a tumor was previously seen to be present by these detection methodologies.

The term "tumor-associated antigen" (TAA) as used herein can be any type of cancer antigen that may be associated with a tumor as is known in the art and includes antigens found on the cell surface, including tumor cells, as well as soluble cancer antigens. Several cell surface antigens on tumors and normal cells have soluble counterparts. Such antigens include, but are not limited to those found on cancer-associated fibroblasts (CAFs), tumor endothelial cells (TEC) and tumor-associated macrophages (TAM). Examples of cancer-associated fibroblasts (CAFs) target antigens include but are not limited to: carbonic anhydrase IX (CAIX); fibroblast activation protein alpha (FAPα); and matrix metalloproteinases (MMPs) including MMP-2 and MMP-9. Examples of Tumor endothelial cell (TECs) target antigens include, but are not limited to vascular endothelial growth factor (VEGF) including VEGFR-1, 2, and 3; CD-105 (endoglin), tumor endothelia markers (TEMs) including TEM1 and TEM8; MMP-2; Survivin; and prostate-specific membrane antigen (PMSA). Examples of tumor associated macrophage antigens include, but are not limited to: CD105; MMP-9; VEGFR-1, 2, 3 and TEM8. According to some embodiments, the tumor associated antigen may be CA125, folate binding protein (FBP), HER2/neu, MUC1 or PSA.

Before describing the present invention in detail, a number of terms will be defined. As used herein, the singular forms "a", "an", and "the" include plural referents unless the context clearly dictates otherwise.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that can or cannot be utilized in a particular embodiment of the present invention.

For the purposes of describing and defining the present invention it is noted that the term "substantially" is utilized herein to represent the inherent degree of uncertainty that can be attributed to any quantitative comparison, value, measurement, or other representation. The term "substantially" is also utilized herein to represent the degree by which a quantitative representation can vary from a stated reference without resulting in a change in the basic function of the subject matter at issue.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

All references cited herein, including published or corresponding U.S. or foreign patent applications, issued U.S. or foreign patents, and any other references, are incorporated by reference in their entireties, including all data, tables, figures, and text presented in the cited references.

BRIEF DESCRIPTION OF THE DRAWINGS

Further features and advantages of the present disclosure will become apparent from the following detailed description, taken in combination with the appended drawings, in which.

DETAILED DESCRIPTION

Figure 1:
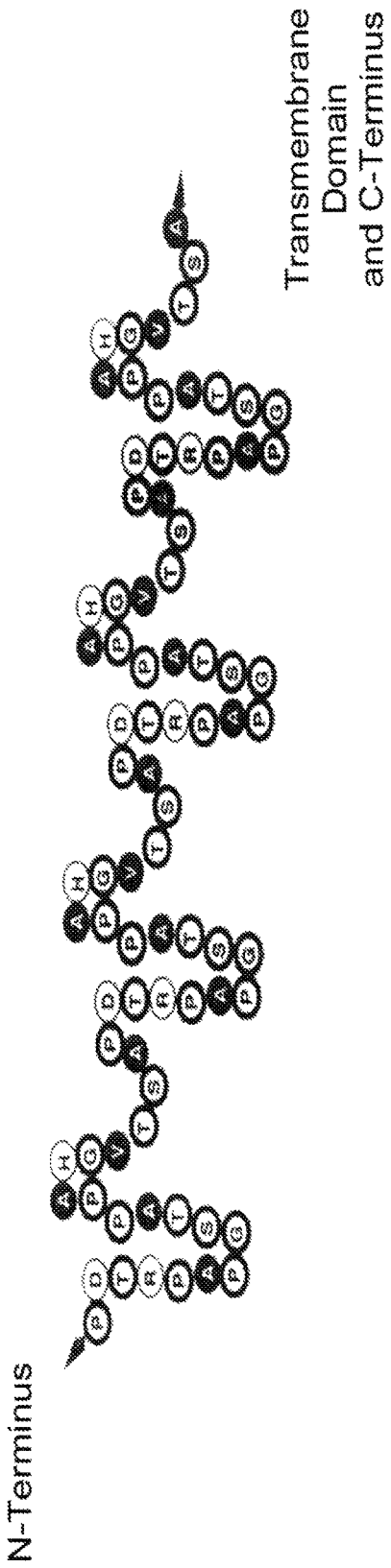
FIG. 1 illustrates the Mucin polypeptide backbone with a Chou-Fasman predicted structural characteristics of the tandem repeat domain.

In embodiments there are disclosed a method for treating cancer in a patient comprising administering to the patient a monoclonal antibody specific for a tumor associated antigen in combination with at least one immunostimulatory compound, and at least one immune homeostatic checkpoint inhibitor.

The inventors have unexpectedly discovered that monoclonal antibody specific for a tumor associated antigen in combination with at least one immunostimulatory compound, and at least one immune homeostatic checkpoint inhibitor can inhibit tumor growth. Without being bound by theory, the combination of monoclonal antibodies specific for a tumor associated antigen with the immunostimulatory compound, and the immune homeostatic checkpoint inhibitor in accordance with the invention appear to be protecting subjects against growth of tumors. The invention is unique and unexpected in that it provides for a synergistic effect between these three immune modulators to greatly reduce and even completely inhibit tumor growth. The end result is that a tumor will grow slowly or even be eliminated. This is in stark contrast to the use of these individual immune effectors alone, which are less efficient at blocking tumor cell growth.

A reduction in growth kinetics, or complete elimination of, a cancer tumor or a metastasized cell or tumor as used herein is defined to mean that which is as understood in the art. For example, a reduction in growth kinetics means a reduction in the exponential growth, specific growth rate, or doubling time of a primary solid tumor, metastasized cell, or metastasized tumor relative to the exponential growth, specific growth rate, or doubling time normally observed in vivo or in vitro for a given tumor type. Complete elimination of a tumor is the absence of tumor presence, either by symptoms, physical exam, or radiographic imaging, in the presence of the therapeutic monoclonal antibody specific for a tumor associated antigen in combination with at least one immunostimulatory compound, and at least one immune homeostatic checkpoint inhibitor, where a tumor was previously seen to be present by these detection methodologies.

According to an embodiment, antigen specific antibodies can be used to enhance T cell reactivity to self-antigens, especially in patients without mutations in human tumor associated antigens (TAA) that are identical with self. By binding self-antigens with low dose immunogenic antibodies, the pool of available tumor specific T cells is enhanced and checkpoint interference can lead to amplified immunity and enhanced clinical activity of the therapy. The use of adjuvants such as TLR3 or TLR4 agonists, in addition to selective chemotherapeutic agents that have been found to stimulate aspects of adaptive immunity, and immune homeostatic checkpoint inhibitors can further enhance this effect.

The combined effect of the immune modulator results in the inhibition of tumor growth and/or the facilitation of tumor destruction, in whole or in part.

A "therapeutic monoclonal antibody specific for a tumor associated antigen" as used in the invention is a monoclonal antibody that may be any suitable monoclonal antibody, such as for example an IgG, and/or an IgE (which comprises the human Fc epsilon (ε) constant region) and also comprises variable regions comprising at least one antigen binding region specific for a tumor-associated antigen (TAA) that is a cell surface antigen or a soluble cancer antigen located in the tumor microenvironment or otherwise in close proximity to the tumor being treated.

In one embodiment, the therapeutic monoclonal antibody specific for a tumor associated antigen may be specific for cancer antigens located on non-tumor cells, for example, VEGFR-2, MMPs, Survivin, TEM8 and PMSA. The cancer antigen may be an epithelial cancer antigen, (e.g., breast, gastrointestinal, lung), a prostate specific cancer antigen (PSA) or prostate specific membrane antigen (PSMA), a bladder cancer antigen, a lung (e.g., small cell lung) cancer antigen, a colon cancer antigen, an ovarian cancer antigen, a brain cancer antigen, a gastric cancer antigen, a renal cell carcinoma antigen, a pancreatic cancer antigen, a liver cancer antigen, an esophageal cancer antigen, or a head and neck cancer antigen. A cancer antigen can also be a lymphoma antigen (e.g., non-Hodgkin's lymphoma or Hodgkin's lymphoma), a B-cell lymphoma cancer antigen, a leukemia antigen, a myeloma (i.e., multiple myeloma or plasma cell myeloma) antigen, an acute lymphoblastic leukemia antigen, a chronic myeloid leukemia antigen, or an acute myelogenous leukemia antigen.

Other cancer antigens include but are not limited to mucin-1 protein or peptide (MUC-1) that is found on most human adenocarcinomas: pancreas, colon, breast, ovarian, lung, prostate, head and neck, including multiple myelomas and some B cell lymphomas; human epidermal growth factor receptor-2 (HER-2/neu) antigen; epidermal growth factor receptor (EGFR) antigen associated lung cancer, head and neck cancer, colon cancer, breast cancer, prostate cancer, gastric cancer, ovarian cancer, brain cancer and bladder cancer; prostate-specific antigen (PSA) and/or prostate-specific membrane antigen (PSMA) that are prevalently expressed in androgen-independent prostate cancers; gp-100 (Glycoprotein 100) associated with melanoma carcinoembryonic (CEA) antigen; carbohydrate antigen 19.9 (CA 19.9) related to the Lewis A blood group substance and is associated with colorectal cancers; and a melanoma cancer antigen such as MART-1.

Other antigens include mesothelin, folate binding protein (FBP), carbohydrate antigen 125 (CA-125) and melanoma associated antigens such as NYESO 1.

In one embodiment, the cancer antigen is a released, soluble version of a cell surface cancer antigen. In a preferred embodiment the tumor-associated target antigen is strictly a cell surface antigen located on the surface of a tumor cells. In one preferred embodiment the tumor associated antigen is selected from CA125, folate binding protein (FBP), HER2/neu, MUC1, and PSA.

The terms "monoclonal antibody" or "monoclonal antibodies" as used herein refer to a preparation of antibodies of single molecular composition. A monoclonal antibody composition displays a single binding specificity and affinity for a particular epitope. The monoclonal antibodies of the present invention are preferably chimeric, humanized, or fully human in order to bind to human antibody receptors such as the human Fc epsilon receptors when the subject host is a human. Humanized and fully human antibodies are also useful in reducing immunogenicity toward the murine components of, for example, a chimeric antibody, when the host subject is human. Monoclonal antibodies may be prepared by standard techniques including, but not limited to, recombinantly and synthetically.

The term "chimeric monoclonal antibody" refers to antibodies displaying a single binding specificity, which have one or more regions derived from one antibody and one or more regions derived from another antibody. In one embodiment of the invention, the constant regions are derived from the human epsilon (ε) constant region (heavy chain) and human kappa or lambda (light chain) constant regions. The variable regions of a chimeric IgE monoclonal antibody of the invention are typically of non-human origin such as from rodents, for example, mouse (murine), rabbit, rat or hamster.

As used herein, "humanized" monoclonal antibodies comprise constant regions that are derived from human epsilon constant region (heavy chain) and human kappa or lambda (light chain) constant regions. The variable regions of the antibodies preferably comprise a framework of human origin and antigen binding regions (CDRs) of non-human origin.

Fully human or human-like antibodies may be produced through vaccination of genetically engineered animals such as mouse lines produced at Amgen) and Bristol-Myers Squibb which contain the human immunoglobulin genetic repertoire and produce fully human antibodies in response to vaccination. Further, the use of phage display libraries incorporating the coding regions of human variable regions which can be identified and selected in an antigen-screening assay to produce a human immunoglobulin variable region binding to a target antigen.

The term "antigen binding region" refers to that portion of an antibody as used in the invention which contains the amino acid residues that interact with an antigen and confer on the antibody its specificity and affinity for the antigen. The antibody region includes the "framework" amino acid residues necessary to maintain the proper confirmation of the antigen binding residues.

An "antigen" is a molecule or portion of a molecule capable of being bound by an antibody, which is additionally capable of inducing an animal to produce antibody capable of binding to an epitope of that antigen. An antigen can have one or more epitopes that are the same or different. In a preferred embodiment, the antibodies of the invention are specific for a single epitope. In one embodiment, the antigen is a capable of being bound by an antibody as used in the invention to form an immune complex that in combination with at least one immunostimulatory compound, and at least one immune homeostatic checkpoint inhibitor, is capable of inhibiting cancer tumor growth. In one embodiment, the antigen, on its own, may not be capable of stimulating an immune response for any number of reasons, for example, the antigen is a "self" antigen, not normally recognized by the immune system as requiring response or the immune system has otherwise become tolerant to the antigen and does not mount an immune response. In another embodiment, the antigen is MUC1.

The term "epitope" is meant to refer to that portion of an antigen capable of being recognized by and bound by an antibody at one or more of the antibody's binding regions. Epitopes generally comprise chemically active surface groupings of molecules such as amino acids or sugar side chains and have specific three dimensional structure characteristics as well as specific charge characteristics. In one embodiment, an epitope of an antigen is a repetitive epitope. In one embodiment an epitope of an antigen is a non-repetitive epitope.

Therefore, in embodiments, the therapeutic monoclonal antibody specific for a tumor associated antigen may be any suitable antibody. According to another embodiment, the therapeutic monoclonal antibody specific for a tumor associated antigen may be any suitable IgG and/or IgE antibody. According to an embodiment, the tumor associated antigen may be CA125, folate binding protein (FBP), HER2/neu, MUC1 or PSA. According to another embodiment, the monoclonal antibody specific for a tumor associated antigen may be for example mAb-AR20.5, mAb-B43.13, mAb 3C6.hIgE, mAb 4H5.hIgE. According to another embodiment, the therapeutic tumor associated antigen specific antibody may be a chimeric monoclonal antibody, a humanized monoclonal antibody or a fully human monoclonal antibody.

Methods for raising antibodies, such as murine antibodies to an antigen, and for determining if a selected antibody binds to a unique antigen epitope are well known in the art.

Screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. Many means are known in the art for detecting binding in an immunoassay and are within the scope of the present invention.

For preparation of monoclonal antibodies, any technique that provides for the production of antibody molecules by continuous cell lines in culture may be used (see, e.g., Antibodies—A Laboratory Manual, Harlow and Lane, eds., Cold Spring Harbor Laboratory Press: Cold Spring Harbor, N.Y., 1988). These include but are not limited to the hybridoma technique originally developed by Kohler and Milstein (1975, Nature 256:495-497), as well as the trioma technique, the human B-cell hybridoma technique (Kozbor et al., 1983, Immunology Today, 4:72), and the EBV-hybridoma technique to produce human monoclonal antibodies (Cole et al., 1985, in Monoclonal Antibodies and Cancer Therapy, Alan R. Liss, Inc., pp. 77-96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. U.S.A., 80:2026-2030) or by transforming human B cells with EBV virus in vitro (Cole et al., 1985, in Monoclonal Antibodies and Cancer Therapy, Alan R. Liss, pp. 77-96). In fact, according to the invention, techniques developed for the production of "chimeric antibodies" (Morrison et al., 1984, J. Bacteriol. 159: 870; Neuberger et al., 1984, Nature 312:604-608; Takeda et al., 1985, Nature 314: 452-454) by splicing the genes from a mouse antibody molecule specific for a polypeptide together with genes from a human antibody molecule of appropriate biological activity can be used; such antibodies are within the scope of this invention.

In one embodiment, the antibody used in the invention is an IgE monoclonal antibody comprising a nucleic acid sequence selected from a heavy chain variable region encoded by a nucleic acid sequence comprising SEQ ID NO: 1; a light chain variable region encoded by a nucleic acid sequence comprising SEQ ID NO: 2 and any combination thereof and wherein the heavy and light chain is grafted onto human epsilon heavy chain and kappa light chain genes, respectively.

In one embodiment the antibody used in the invention is an IgE monoclonal antibody comprising a nucleic acid sequence selected from a heavy chain variable region encoded by the nucleic acid of SEQ ID NO: 3; a light chain variable region encoded by the nucleic acid of SEQ ID NO: 4 and any combination thereof and wherein the heavy and light chain is grafted onto human epsilon heavy chain and kappa light chain genes, respectively.

In one embodiment, the invention provides a monoclonal antibody, 3C6.hIgE, comprising variable regions of the light and heavy chain of IgG cloned from the VU-3C6 hybridoma, and grafted onto human Ig kappa light chain and epsilon heavy chain genes, respectively. VU-3C6 targets human mucin 1 (hMUC1), a hypoglycosylated form of mucin overexpressed on tumors arising from glandular epithelium. In one embodiment, the invention comprises the IgE antibody, 4H5.hIgE, which is specific to an isoform of MUC1 different from the MUC1 isoform that 3C6.hIgE is specific to.

In one embodiment, the antibody of the invention is the monoclonal antibody 3C6.hIgE comprising a heavy chain variable region encoded by a nucleic acid sequence comprising SEQ ID NO: 1; a light chain variable region encoded by a nucleic acid sequence comprising SEQ ID NO: 2.

In one embodiment the antibody of the invention is the monoclonal antibody 4H5.hIgE. The antibody 4H5.hIgE has a heavy chain variable region encoded by the nucleic acid of SEQ ID NO: 3 and a light chain variable region encoded by the nucleic acid of SEQ ID NO: 4 and grafted onto human Ig kappa light chain and epsilon heavy chain genes.

In one embodiment, the therapeutic monoclonal antibody specific for a tumor associated antigen is an IgG monoclonal antibody specific for an epitope of MUC1. In one embodiment, the IgG monoclonal antibody is antibody AR20.5, as disclosed in Qi, W, et al.; Hybrid Hybridomics. 2001; 20(5-6):313-24. MAb AR20.5 reacts strongly with either the soluble form or the cell surface epitope of MUC1 on many human cancer cell lines. In one embodiment, the antibody of the invention is specific for the epitope of MUC1 comprising amino acids STAPPAHGVTSAPDTRPAPG [SEQ ID NO: 5] of MUC1. The exact epitope lies in one of the 20 amino acid repeats that characterize the external domain of MUC1. In one embodiment, the antibody of the invention is capable of binding MUC1 at the epitope defined at STAPPAHGVTSAPDTRPAPG [SEQ ID NO: 5].

In one embodiment, the therapeutic monoclonal antibody specific for a tumor associated antigen is an IgE monoclonal antibody specific for an epitope of MUC1. In one embodiment, the antibody of the invention is specific for the epitope of MUC1 comprising amino acids STAPPAHGVTSAP-DTRPAPG [SEQ ID NO: 5] of MUC1. The exact epitope lies in one of the 20 amino acid repeats that characterize the external domain of MUC1. In one embodiment, the antibody of the invention is capable of binding MUC1 at the epitope defined at STAPPAHGVTSAPDTRPAPG [SEQ ID NO: 5].

In one embodiment, therapeutic monoclonal antibodies specific for a tumor associated antigen in accordance with the present invention are expressed by a positive transfectoma which is identified by enzyme-linked immunosorbent assay (ELISA) and Western Blot. The positive transfectoma will be cloned by limited dilution for highest productivity and selected for antibody production. As used herein a "transfectoma" includes recombinant eukaryotic host cells expressing the antibody, such as Chinese hamster ovary (CHO) cells and NS/O myeloma cells. Such transfectoma methodology is well known in the art (Morrison, S. (1985) Science, 229:1202). Previously published methodology used to generate mouse/human chimeric or humanized antibodies has yielded the successful production of various human chimeric antibodies or antibody fusion proteins (Helguera G, Penichet ML., Methods Mol. Med.(2005) 109:347-74).

In general, chimeric mouse-human monoclonal antibodies (i.e., chimeric antibodies) can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted. (See Robinson et al., International Patent Publication PCT/US86/02269; Akira, et al., European Patent Application 184,187; Taniguchi, M., European Patent Application 171, 496; Morrison et al., European Patent Application 173,494; Neuberger et al., International Application WO 86/01533; Cabilly et al. U.S. Pat. No. 4,816,567; Cabilly et al., European Patent Application 125,023; Better et al. (1988 Science, 240:1041-1043); Liu et al. (1987) PNAS, 84:3439-3443; Liu et al., 1987, J. Immunol., 139:3521-3526; Sun et al. (1987) PNAS, 84:214-218; Nishimura et al., 1987, Canc. Res., 47:999-1005; Wood et al. (1985) Nature, 314:446-449; and Shaw et al., 1988, J. Natl Cancer Inst., 80:1553-1559).

The chimeric antibody can be further humanized by replacing sequences of the Fv variable region which are not directly involved in antigen binding with equivalent sequences from human Fv variable regions. General reviews of humanized chimeric antibodies are provided by Morrison, S. L., 1985, Science, 229:1202-1207 and by Oi et al., 1986, BioTechniques, 4:214. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from 7E3, an anti-GPII$_b$III$_a$ antibody producing hybridoma. The recombinant DNA encoding the chimeric antibody, or fragment thereof, can then be cloned into an appropriate expression vector. Suitable humanized antibodies can alternatively be produced by CDR substitution (U.S. Pat. No. 5,225,539; Jones et al. 1986 Nature, 321:552-525; Verhoeyan et al. 1988 Science, 239: 1534; and Beidler et al. 1988 J. Immunol., 141:4053-4060).

As used herein, an "effective amount" of a therapeutic monoclonal antibody specific for a tumor associated antigen of the invention is that amount sufficient to recognize and bind the epitope of the TAA that is a cell surface antigen and induce, elicit, or enhance the referenced immune response in accordance with the invention.

According to an embodiment, the present invention includes immunostimulatory compounds. Immunostimulatory compounds are compound having the capacity to stimulate or elicit an immune response. As used herein, the term relates to exemplary immunostimulatory compounds that include toll-like receptor (TLR) agonists (e.g., TLR3, TLR4, TLR7, TLR9), N-acetylmuramyl-L-alanine-D-isoglutamine (MDP), lipopolysaccharides (LPS), genetically modified and/or degraded LPS, alum, glucan, colony stimulating factors (e.g., EPO, GM-CSF, G-CSF, M-CSF, pegylated G-CSF, SCF, IL-3, IL6, PIXY 321), interferons (e.g., gamma-interferon, alpha-interferon), interleukins (e.g., IL-2, IL-7, IL-12, IL-15, IL-18), MHC Class II binding peptides, saponins (e.g., QS21), unmethylated CpG sequences, 1-methyl tryptophan, arginase inhibitors, cyclophosphamide, antibodies that block immunosuppressive functions (e.g., anti-CTLA4 antibodies, anti-TGF-beta, etc.), and mixtures of two or more thereof.

In one preferred embodiment the immunostimulatory compound is a TLR3 agonist. In preferred embodiments, the TLR3 agonist for use according to the invention is a double stranded nucleic acid selected from the group consisting of: polyinosinic acid and polycytidylic acid, polyadenylic acid and polyuridylic acid, polyinosinic acid analogue and polycytidylic acid, polyinosinic acid and polycytidylic acid analogue, polyinosinic acid analogue and polycytidylic acid analogue, polyadenylic acid analogue and polyuridylic acid, polyadenylic acid and polyuridylic acid analogue, and polyadenylic acid analogue and polyuridylic acid analogue. Specific examples of double-stranded RNA as TLR3 agonists further include Polyadenur (Ipsen) and Ampligen (Hemispherx). Polyadenur is a polyA/U RNA molecule, i.e., contains a polyA strand and a polyU strand. Ampligen is disclosed for instance in EP 281 380 or EP 113 162. In another preferred embodiment, the TLR3 agonist may be polyIC or polyICLC (Hiltonol®), which is a synthetic complex of carboxymethylcellulose, polyinosinic-polycytidylic acid, and poly-L-lysine double-stranded RNA. Poly (I:C)LC may stimulate the release of cytotoxic cytokines and, by inducing interferon-gamma production, may increase the tumoricidal activities of various immunohematopoietic cells.

In one embodiment the immunostimulatory compound is a TLR4 agonist. Exemplary TLR4 agonists include taxanes such as paclitaxel and docetaxal, lipopolysaccharides (LPS); E. coli LPS; and P. gingivalis LPS.

As used herein, an "effective amount" of an immunostimulatory compound of the invention is that amount sufficient to induce, elicit, or enhance the referenced immune response in accordance with the invention.

According to another embodiment, the present invention includes immune homeostatic checkpoint inhibitors. Immune homeostatic checkpoint inhibitors are monoclonal antibodies (mAb) directed to immune checkpoint molecules, which are expressed on immune cells and mediate signals to attenuate excessive immune reactions. According to an embodiment, immune homeostasis checkpoint inhibition may be performed with inhibitory monoclonal antibodies directed at the inhibitory immune receptors CTLA-4, PD-1, and PDL-1. According to some embodiments, such inhibitors have emerged as successful treatment approaches for patients with advanced melanoma. According to an embodiment, the immune homeostatic checkpoint inhibitors may be one of an anti-CTLA-4, anti-PD-1, and/or anti-PDL-1 antibody. According to an embodiment, the anti-CTLA-4 antibody may be Ipilimumab or tremelimumab or combinations thereof. According to another embodiment, the anti-PDL-1 antibody may be B7-H1 antibody, BMS-936559 antibody, MPDL3280A (atezolizumab) antibody, MEDI-4736 antibody, MSB0010718C antibody or combinations thereof. According to another embodiment, the anti-PD-1 antibody may be Nivolumab antibody, pembrolizumab antibody, pidilizumab antibody or combinations thereof. In addition, PD-1 may also be targeted with AMP-224, which is a PD-L2-IgG recombinant fusion protein. Additional antagonists of inhibitory pathways in the immune response are being advanced through clinical development. IMP321 is a soluble LAG-3 Ig fusion protein and MHC class II agonist, which is used to increase an immune response to tumors. LAG3 is an immune checkpoint molecule. Lirilumab is an antagonist to the KIR receptor and BMS 986016 is an antagonist of LAG3. A third inhibitory checkpoint pathway is the TIM-3-Galectin-9 pathway that is also a promising target for checkpoint inhibition. RX518 targets and activates the glucocorticoid-induced tumor necrosis factor receptor (GITR), a member of the TNF receptor superfamily that is expressed on the surface of multiple types of immune cells, including regulatory T cells, effector T cells, B cells, natural killer (NK) cells, and activated dendritic cells.

As used herein, an "effective amount" of an immune homeostatic checkpoint inhibitor of the invention is that amount sufficient to induce, elicit, or enhance the referenced immune response in accordance with the invention.

According to another embodiment, the method of the present invention comprises the steps of
a) administering a therapeutically effective amount of the therapeutic monoclonal antibody specific for a tumor associated antigen;
b) administering a therapeutically effective amount of the immunostimulatory compound after step a); and
c) administering a therapeutically effective amount of the immune homeostatic checkpoint inhibitor, after step b).

In one embodiment, step b) may be performed 1 or more days after step a). In another embodiment, step c) may be performed 1 or more days after step b).

According to another embodiment, the method of the present invention comprises the steps of
a) administering a therapeutically effective amount of the therapeutic monoclonal antibody specific for a tumor associated antigen;
b) administering a therapeutically effective amount of the immune homeostatic checkpoint inhibitor after step a); and
c) administering, a therapeutically effective amount of the immunostimulatory compound after step b).

In one embodiment, step b) may be performed 1 or more days after step a). In another embodiment, step c) may be performed 1 or more days after step b).

According to another embodiment, the method of the present invention comprises the steps of
a) administering a therapeutically effective amount of the immunostimulatory compound
b) administering a therapeutically effective amount of the therapeutic monoclonal antibody specific for a tumor associated antigen after step a); and
c) administering a therapeutically effective amount of the immune homeostatic checkpoint inhibitor, after step b).

In one embodiment, step b) may be performed 1 or more days after step a). In another embodiment, step c) may be performed 1 or more days after step b).

According to another embodiment, the method of the present invention comprises the steps of
a) administering a therapeutically effective amount of the immunostimulatory compound;
b) administering a therapeutically effective amount of the immune homeostatic checkpoint inhibitor after step a); and
c) administering a therapeutically effective amount of the therapeutic monoclonal antibody specific for a tumor associated antigen, after step b).

In one embodiment, step b) may be performed 1 or more days after step a). In another embodiment, step c) may be performed 1 or more days after step b).

According to another embodiment, the method of the present invention comprises the steps of
a) administering a therapeutically effective amount of the immune homeostatic checkpoint inhibitor;
b) administering a therapeutically effective amount of the therapeutic monoclonal antibody specific for a tumor associated antigen after step a); and
c) administering a therapeutically effective amount of the immunostimulatory compound, after step b).

In one embodiment, step b) may be performed 1 or more days after step a). In another embodiment, step c) may be performed 1 or more days after step b).

According to another embodiment, the method of the present invention comprises the steps of
a) administering a therapeutically effective amount of the immune homeostatic checkpoint inhibitor;
b) administering a therapeutically effective amount of the immune homeostatic checkpoint inhibitor after step a); and
c) administering a therapeutically effective amount of the therapeutic monoclonal antibody specific for a tumor associated antigen, after step b).

In one embodiment, step b) may be performed 1 or more days after step a). In another embodiment, step c) may be performed 1 or more days after step b).

According to another embodiment, the present invention also encompasses the use of a therapeutic monoclonal antibody specific for a tumor associated antigen in combination with at least one immunostimulatory compound, and at least one immune homeostatic checkpoint inhibitor for inhibiting cancer tumor growth in a patient in need thereof.

In embodiments, the use employs the therapeutic monoclonal antibody specific for a tumor associated antigen in combination with at least one immunostimulatory compound, and at least one immune homeostatic checkpoint inhibitor as described above for inhibiting cancer tumor growth in a patient in need thereof According to yet another embodiment, the present invention also encompasses composition for use for inhibiting cancer tumor growth in a patient in need thereof, the composition comprising a therapeutic monoclonal antibody specific for a tumor associated antigen, at least one immunostimulatory compound, and at least one immune homeostatic checkpoint inhibitor.

Such compositions comprise a therapeutically effective amount of a therapeutic monoclonal antibody specific for a tumor associated antigen, at least one immunostimulatory compound, and at least one immune homeostatic checkpoint inhibitor and may also include a pharmaceutically acceptable carrier. In one preferred embodiment, the pharmaceutical composition comprises a therapeutic IgE monoclonal antibody that specifically binds a single epitope of MUC1.

In accordance with a method or use of the invention compositions comprising the therapeutic monoclonal antibody specific for a tumor associated antigen, the immunostimulatory compound, and the immune homeostatic checkpoint inhibitor of the invention may be administered to the patient by any immunologically suitable route. For example, they may be introduced into the patient by an intravenous, subcutaneous, intraperitoneal, intrathecal, intravesical, intradermal, intramuscular, or intralymphatic routes, alone or as combination. The composition may be in solution, tablet, aerosol, or multi-phase formulation forms. Liposomes, long-circulating liposomes, immunoliposomes, biodegradable microspheres, micelles, or the like may also be used as a carrier, vehicle, or delivery system. Furthermore, using ex vivo procedures well known in the art, blood or serum from the patient may be removed from the patient; optionally, it may be desirable to purify the antigen in the patient's blood; the blood or serum may then be mixed with a composition that includes a binding agent according to the invention; and the treated blood or serum is returned to the patient. The invention should not be limited to any particular method of introducing the binding agent into the patient.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the composition of the invention which will be effective in the treatment, inhibition and prevention of tumor growth associated with the antigen to which the antibody of the invention is specific can be determined by standard clinical techniques. The presence of the antibody in the extra vascular space, can be assayed by standard skin wheal and flair responses, in response to intradermal administration of purified antigen (e.g. MUC1). In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For the antibodies used in the invention, the dosage administered to a patient is typically 0.001 μg/kg to 1 mg/kg of the patient's body weight. Preferably, the dosage administered to a patient is between 0.01 μg/kg and 0.1 mg/kg of the patient's body weight, more preferably 0.02 μg/kg to 20 μg/kg of the patient's body weight. Lower dosages of the antibodies of the invention and less frequent administration may also be possible.

For the immunostimulatory compound used in the invention, the dosage administered to a patient may be according to the ranges or concentrations that have been optimized by their respective manufacturers.

For the immune homeostatic checkpoint inhibitor used in the invention, the dosage administered to a patient may be according to the ranges or concentrations that have been optimized by their respective manufacturers.

The pharmaceutical compositions of the present invention have in vitro and in vivo diagnostic and therapeutic utilities. For example, these molecules can be administered to cells in culture, e.g., in vitro or ex vivo, or in a subject, e.g., in vivo, to treat cancer. As used herein, the term "subject" is intended to include human and non-human animals. A preferred subject is a human patient with cancer. As used herein the terms "treat" "treating" and "treatment" of cancer includes: preventing the appearance of tumor metastasis in a patient, inhibiting the onset of cancer in a patient; eliminating or reducing a preexisting tumor burden in a patient either with metastatic cancer or cancer localized to the organ of origin; prolonging survival in a cancer patient; prolonging the remission period in a cancer patient following initial treatment with chemotherapy and/or surgery; and/or prolonging any period between cancer remission and cancer relapse in a patient.

When used for therapy for the treatment of cancer, the antibodies used in the invention are administered to the patient in therapeutically effective amounts (i.e. amounts needed to treat clinically apparent tumors, or prevent the appearance of clinically apparent tumor, either at the original site or a distant site, at some time point in the future). The antibodies used in the invention and the pharmaceutical compositions containing them will normally be administered parenterally, when possible, or at the target cell site, or intravenously.

According to yet another embodiment, the present invention also encompasses kits for use for inhibiting cancer tumor growth in a patient in need thereof. The kits may comprise a therapeutic monoclonal antibody specific for a tumor associated antigen, at least one immunostimulatory compound, at least one immune homeostatic checkpoint inhibitor, and instructions on how to use the kit.

The present invention will be more readily understood by referring to the following examples which are given to illustrate the invention rather than to limit its scope.

EXAMPLE 1

In Vivo Tumor Challenge Studies in Mice Immunized by Antigen Specific IgG and Combinations In order to first establish the principle of this therapeutic approach, an antibody with suitable specificity and tumor antigen expressing tumor model to be evaluated in an animal tolerant to that tumor antigen are required. A Panc02 tumor cell line transfected with the human MUC1 gene (panc02.muc1) is selected. The panc02 tumors are syngeneic to BL6 mice and the panc02.muc1 is fully syngeneic to the BL6.Tg mice transgenic for human MUC1. The antibody used for the demonstration experiment is mAb-AR20.5 from Quest PharmaTech, a murine monoclonal antibody previously demonstrated to induce immunity to its ligand MUC1 in multiple experimental systems. AR20.5 is an IgG 1κ monoclonal antibody that binds to the sequence DTRPAP in the Core Tandem Repeat of MUC1 (See FIG. 1).

Experimental Design

1) MUC1.Tg animals (i.e. immunologically tolerant to MUC1): all animals are challenged with $1\times10^6$ Panc02.MUC1 cells subcutaneously.

2) mAb-AR20.5 (100 μg) is injected IV at days 7, 17, 27 and every 10 days thereafter until disease progression or 47 days.

3) 50 µg PolyICLC (Hiltonol®) is given IV 7 days post tumor challenge, then at day 12, day 17, day 22, and every 5 days until disease progression or 47 days.

4) 200 µg anti-PDL-1 (clone 10F.9G2 BioXL) is given IP at days 8, 10, 13, 15, 18, 20, 23, 25, and the same cycle (one day and three days post Hiltonol®) until disease progression or 47 days.

Figure 2:
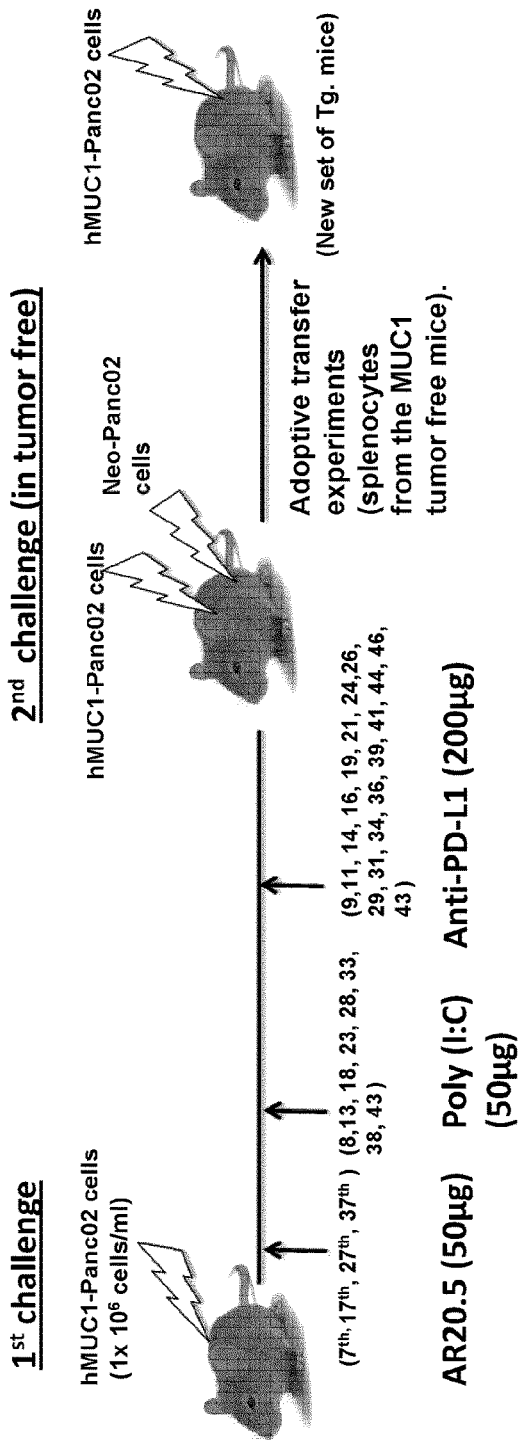
FIG. 2 illustrates the experimental design for the use of the combination of an antigen specific IgG with TLR3 agonists and checkpoint inhibitors.

See FIG. 2 for an illustration of the experimental design of the present example and the rechallenge for mice showing tumor resistance in example 2.

Figure 3:
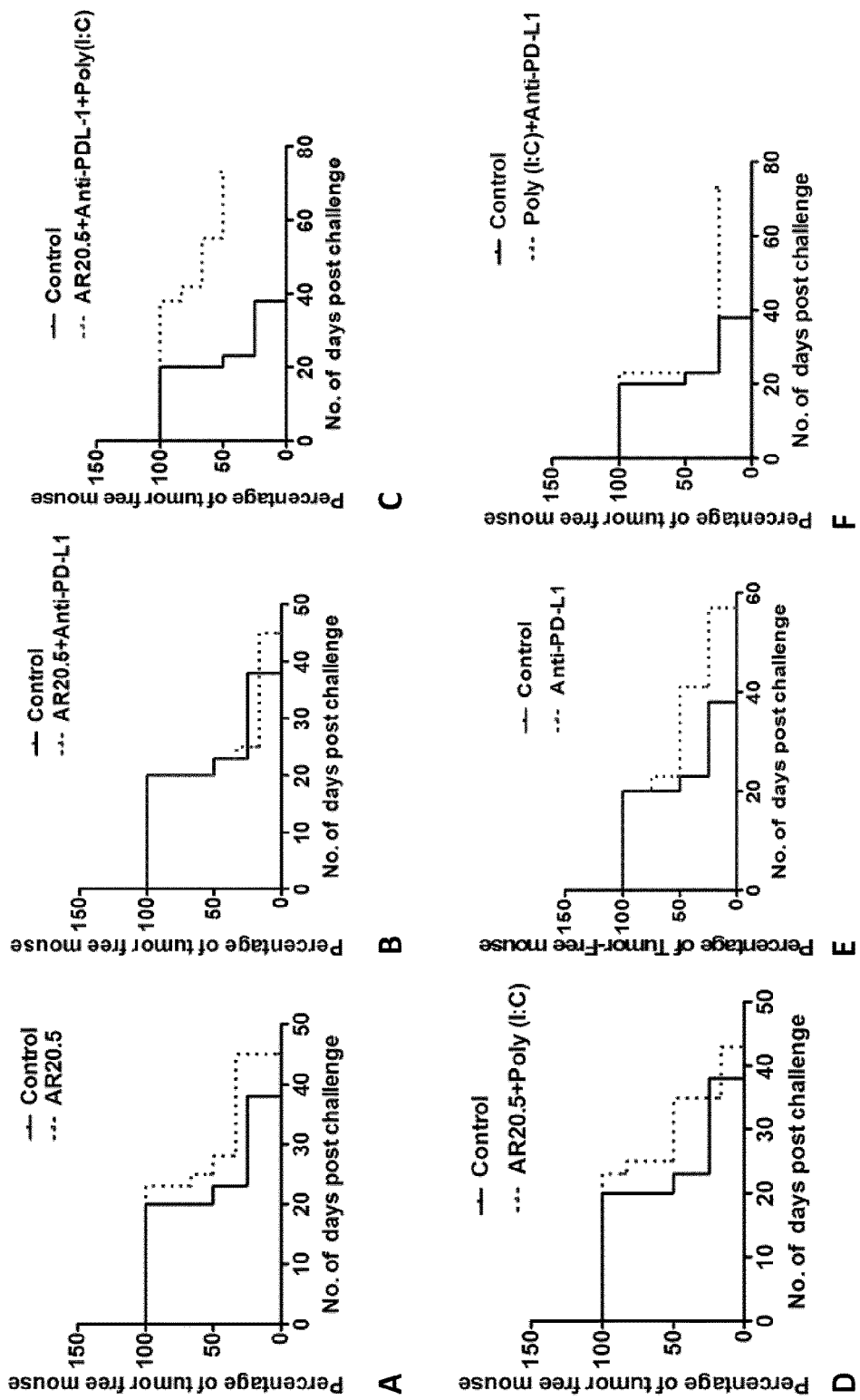
FIG. 3 illustrates the time to tumor appearance post $1^{st}$ challenge with MUC1-Panc02 tumors cells for a third group of animals. Treatment with A) AR20.5 alone, versus control; B) AR20.5 and anti-PDL-1, versus control; C) AR20.5, anti-PDL-1 and PolyICLC, versus control; D) AR20.5 and PolyICLC, versus control; E) anti-PDL-1 alone, versus control; F) anti-PDL-1 and PolyICLC, versus control. Full line represents control, while dashed line represents treatment conditions.
Figure 4:
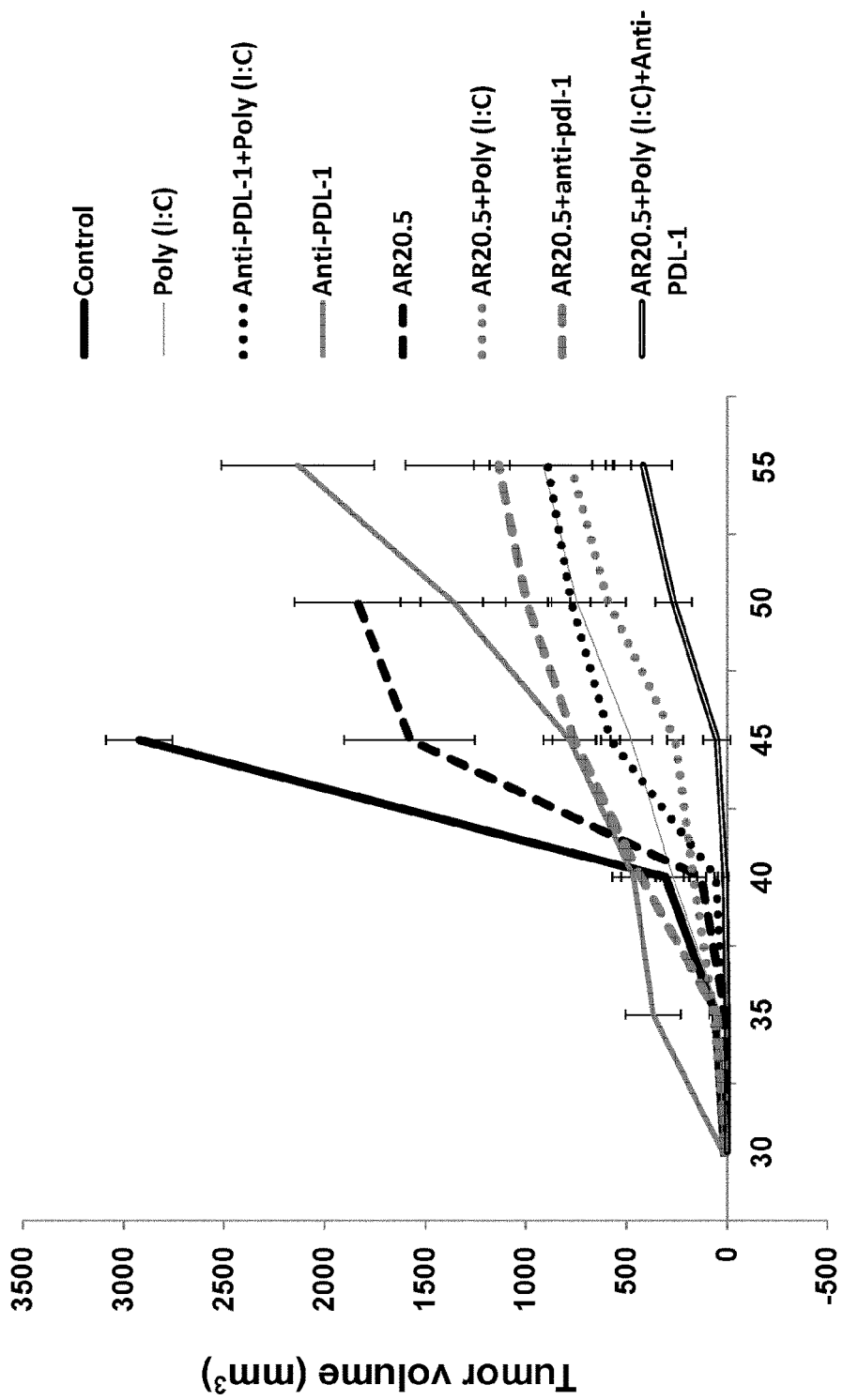
FIG. 4 illustrates the tumor growth curves for different treatment groups post $1^{st}$ challenge with MUC1-Panc02. The tumor volume is plotted over time, over a period of 55 days.

The results of the experiment plotted by percent tumor free over time (FIG. 3) and measured tumor volume over time (FIG. 4). A dramatic treatment effect of the combinatorial therapy using AR20.5 and TLR3 stimulation in conjunction with anti-PDL-1 is observed. These results show a potent interaction between the three immune modulators [anti-MUC1 AR20.5, anti-PDL-1, and PolyICLC], and demonstrate an unexpectedly potent tumor growth inhibitory effect and anti-tumor effect.

EXAMPLE 2

Rechallenge of Tumor Resistant Animals to Confirm Immune Memory and Specificity

Animals from the primary challenge experiment (example 1) that showed no disease progression at day 47 days received no further treatment and were observed for 30 additional days (to 77 days). If there was still no tumor growth, these surviving animals were re-challenged in one flank with Panc02.MUC1 ($1 \times 10^6$) and in the other flank with control Panc02 cells ($1 \times 10^6$) not expressing MUC1, to determine if there is a memory response to MUC1, and whether there is evidence of epitope spreading or general immunity to other tumor antigens on Panc02 cells. Re-challenged animals were observed for up to 60 additional days for evidence of tumor growth (137 days post primary challenge and 60 days post-secondary tumor challenge). (see again FIG. 2 for schema)

Figure 5:
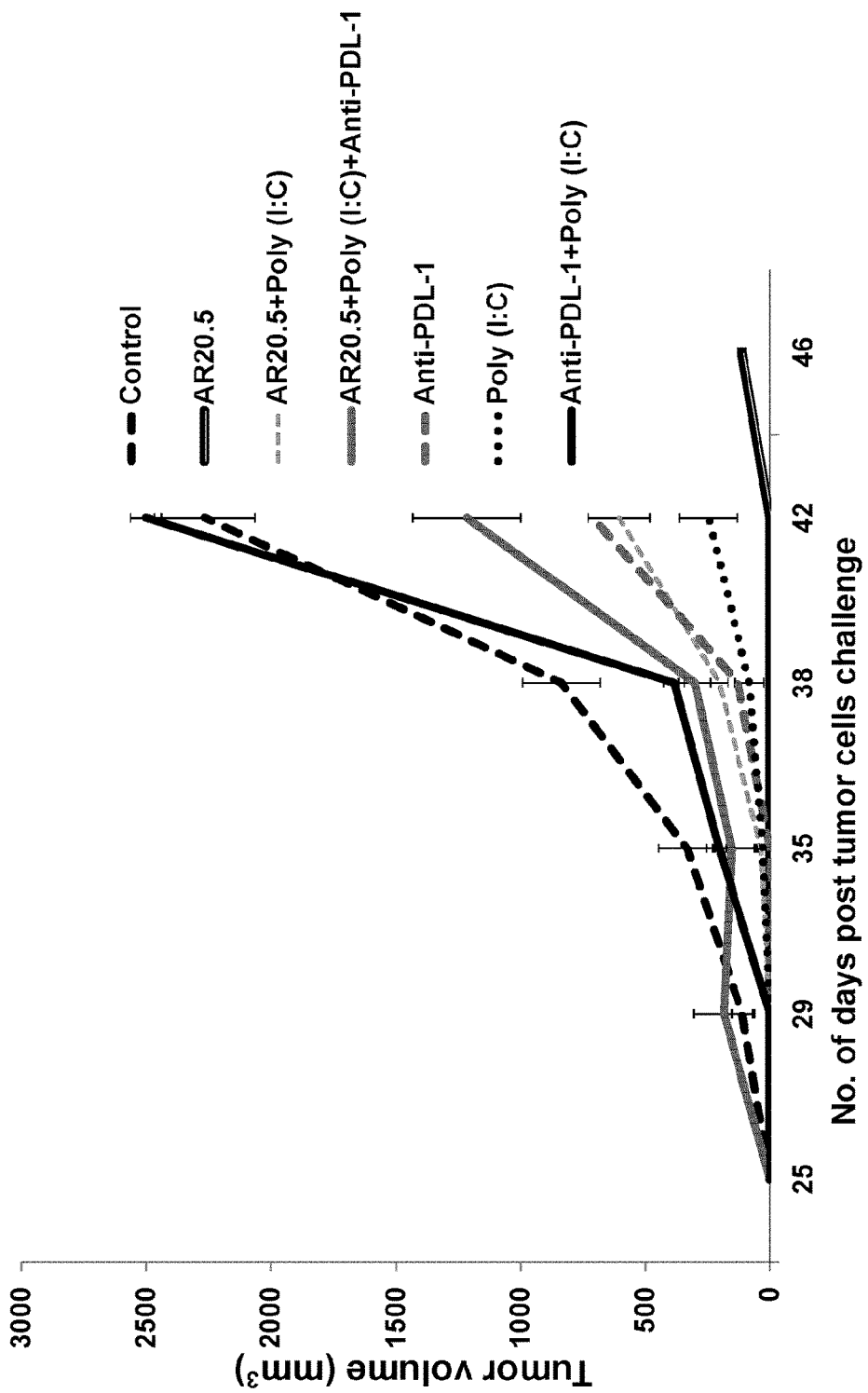
FIG. 5 illustrates the tumor growth curves for surviving mice from different treatment groups following re-challenge with MUC1-Panc02. The tumor volume from the MUC-1-Panco-2 challenged flank is plotted over a period of 46 days.
Figure 6:
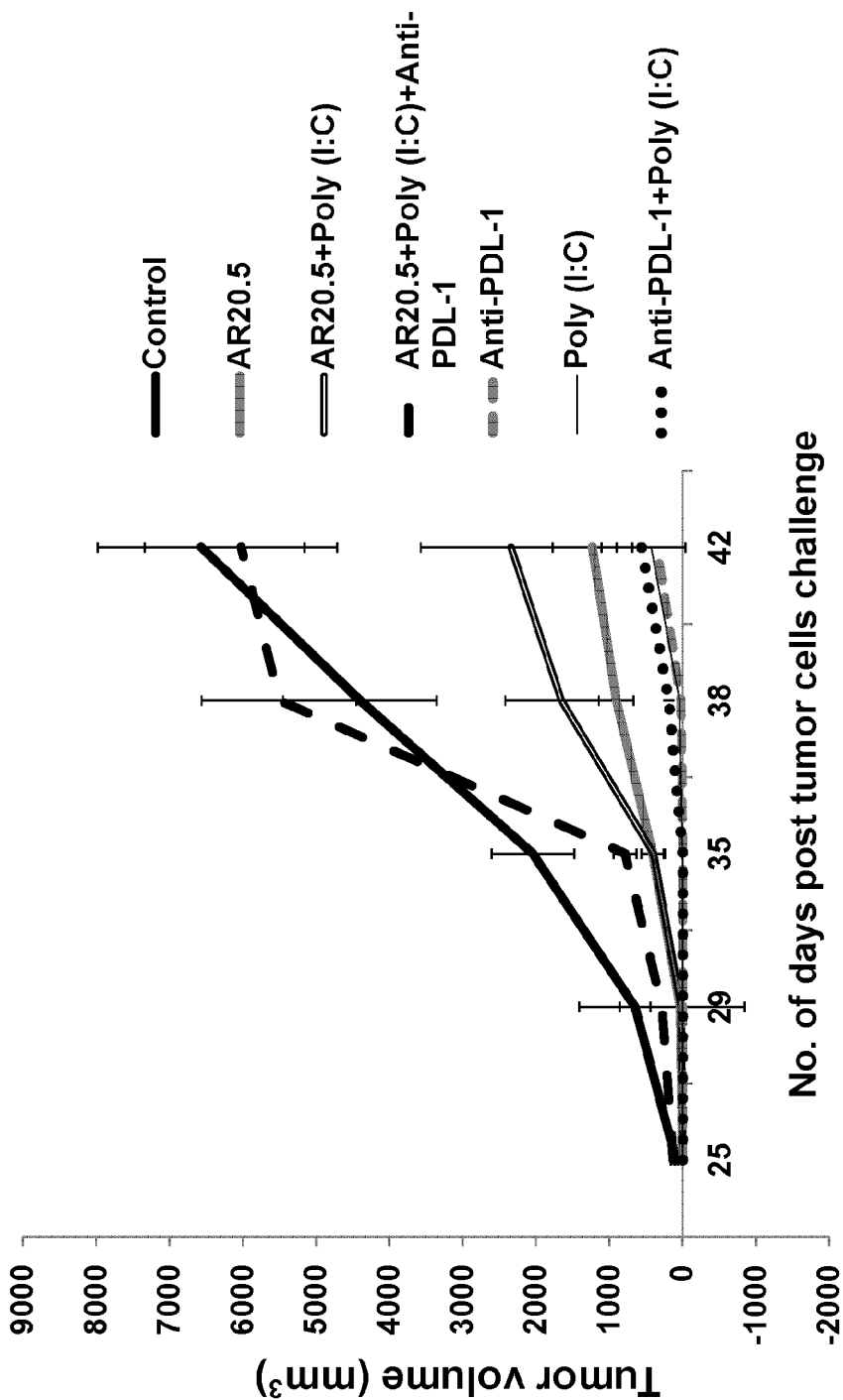
FIG. 6 illustrates the tumor growth curves for surviving mice from different treatment following re-challenge with Neo-Panc02 in the opposite flank. The tumor volume from the neo-panc02 over a period of 46 days.
Figure 7:
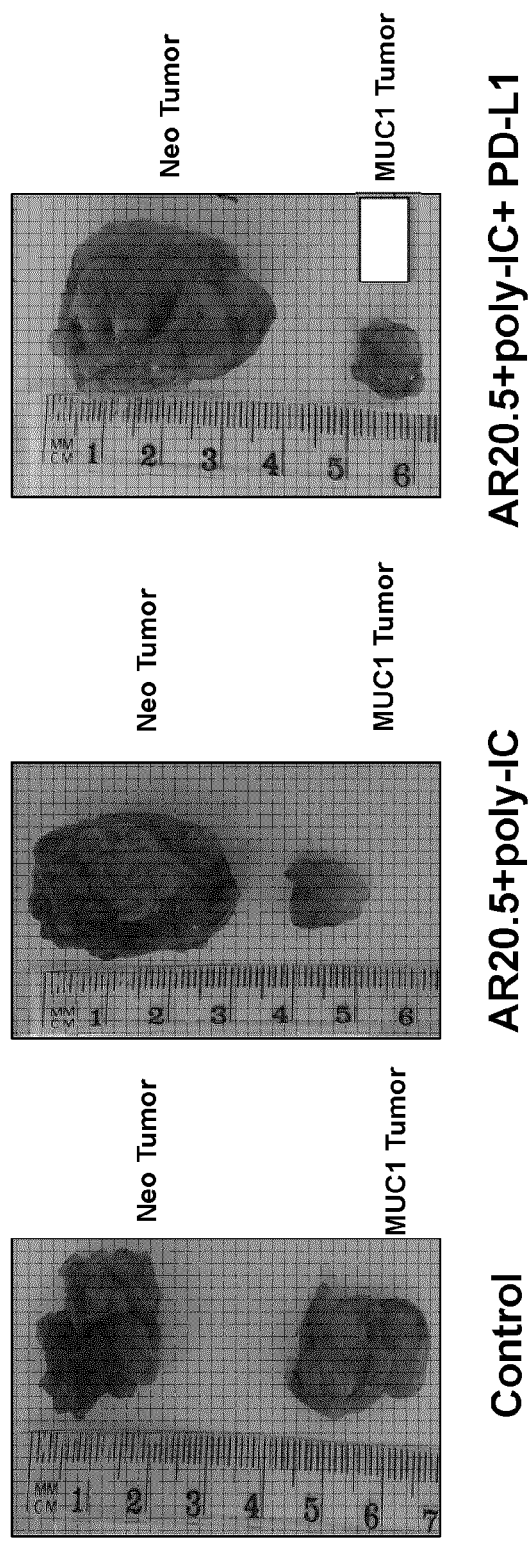
FIG. 7 illustrates images of MUC1 and neo-control tumors from mice re-challenged having resisted primary tumor challenge with combination treatment. A control mouse shows the comparability of MUC1-panco2 and neo-panco-2 tumors growing in a non-immunized animal. In the treated mice the immune resistance tumors that do not express MUC1 (Neo Tumor) grow faster than tumor cells that express MUC1 (MUC1 tumor) confirming the antigen specificity of the prior immunization with AR20.5 and PolyICLC or AR20.5, PolyICLC and anti-PDL-1.

A notable proportion of these mice exhibited antigen-specific rejection of MUC1-Panc02 cells but did not reject antigen negative neo control tumor cells from the opposite flank (FIGS. 5-6). Moreover, in examples of mice that failed to completely reject a second round of MUC1-Panc02 cell challenge, they generated significantly smaller MUC-1 tumors (6.0 mm×3.8 mm×4.8 mm) that did not progress as compared to control tumor (18.9 mm×21.3 mm×22.3 mm) after 50 days of tumor cell challenge (see FIG. 7).

EXAMPLE 3

Splenocytes Transfer from Tumor-Immune Mice

Figure 8:
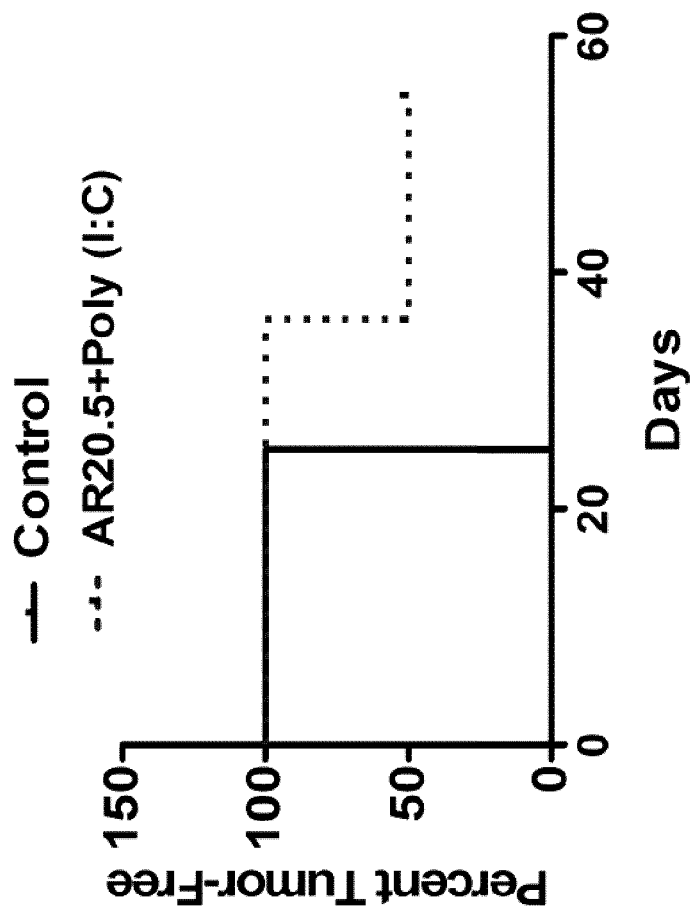
FIG. 8 illustrates the adoptive transfer of splenocytes from a mouse that received AR20.5, antiPDL-1, and PolyICLC combinatorial treatment and rejected primary tumor challenge into two MUC-1 transgenic mice. The mice were challenged with MUC1-Panc02 tumors and followed for appearance of tumor. An untreated mouse served as the control for this challenge. The experiment confirms that that the splenocytes convey tumor resistance.

Splenocytes from a tumor-immune mice that had been immunized with the AR20.5+PolyICLC+Anti-PDL-1 combination were harvested and cultured for five days and then transferred into two fresh MUC1.Tg transgenic mice through tail vein injection. Post transfer, the mice were challenged with $2 \times 10^6$ cells/ml MUC1-Panc02 cells monitored the growth of tumor for additional days. A control mouse that had not received prior treatment or primary challenge also received the same challenge in both flanks. The results are shown in FIG. 8. One of the two mice receiving the transferred splenocytes completely resisted the tumor challenge and in the second mouse the appearance of tumor was delayed relative to the untreated control mouse.

The experiment confirms that tumor specific resistance resides in the splenic compartment.

EXAMPLE 4

Use of Combinations of Antigen Specific IgE with TLR3 Agonists and Checkpoint Inhibitors Double human transgenic C57BL6/J mice carrying the human transgenes for both human MUC1 and the human FcεR alpha chain were inoculated subcutaneously with a total of $10^6$ cells from syngeneic rat pancreatic tumor cell line humuc1-Panc02 transfectoma's (expressing human MUC1). Subcutaneous nodules containing tumors appeared within 3 weeks of injection in this model and are followed for growth until animals are sacrificed per institutional animal care requirements.

Combinatorial Treatments included: anti-MUC1 IgE (20 µg/injection) at days 7, 17, 27 and 37, PolyICLC (50 µg/infusion) at day 8, 13, 18, 23, 28, 33, 38, 43; and anti-PDL-1 (200 µg per injection) at days 9, 11, 14, 16, 19, 21, 24, 24, 26, 29, 31, 34, 36, 39, 41, 44. Eight groups of mice were treated with n=8/group. The groups were: 1=control; 2=anti-PDL-1; 3=PolyICLC; 4=anti-PDL-1 and PolyICLC; 5=anti-MUC1 IgE alone; 6=anti-MUC1 IgE and PolyICLC; 7=anti-MUC1 IgE and anti-PDL-1; and 8=anti-MUC1 IgE and both PolyICLC and anti-PDL-1.

Figure 9:
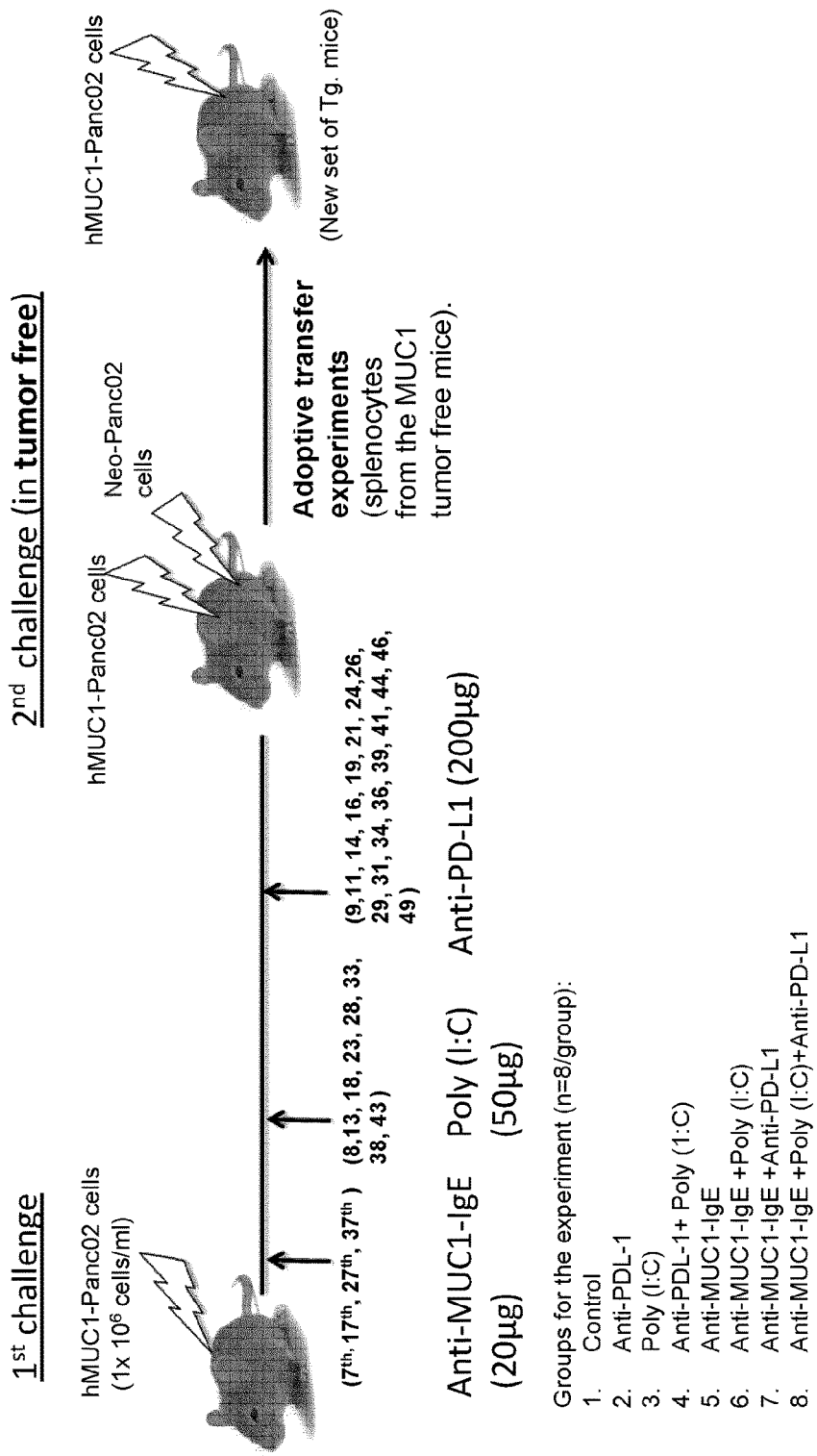
FIG. 9 illustrates the experimental design for the use of the combination of an antigen specific IgE with TLR3 agonists and checkpoint inhibitors.
Figure 10:
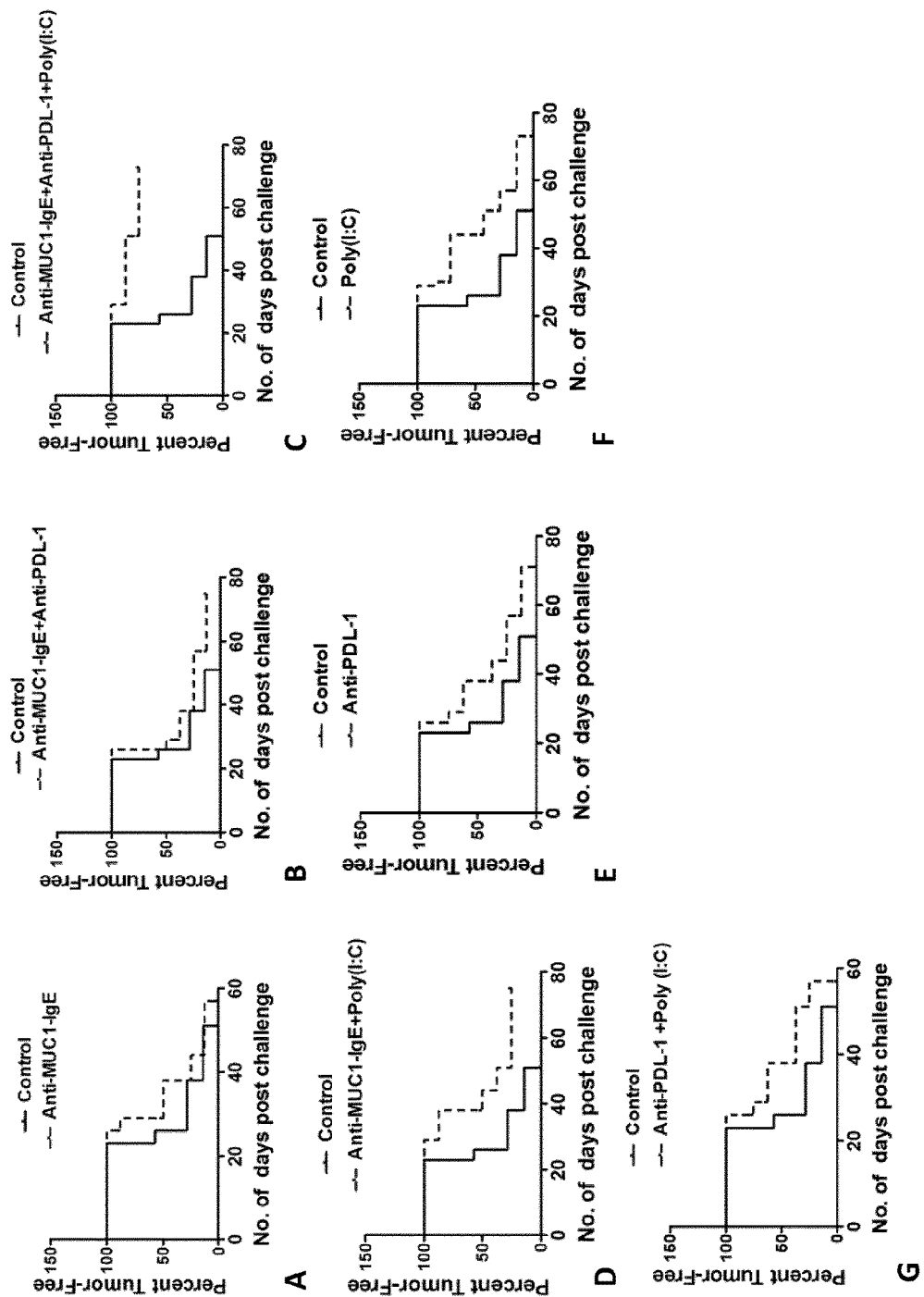
FIG. 10 illustrates the time to tumor appearance post $1^{st}$ challenge with MUC1-Panc02 tumors cells. Treatment with A) anti-MUC1 IgE alone, versus control; B) anti-MUC1 IgE and anti-PDL-1, versus control; C) anti-MUC1 IgE, anti-PDL-1 and PolyICLC versus control; D) anti-MUC1 IgE, and PolyICLC, versus control; E) anti-PDL-1 alone, versus control; F) PolyICLC alone, versus control; and G) anti-PDL-1 and PolyICLC, versus control. Full line represents control, while dashed line represents treatment condition.
Figure 11:
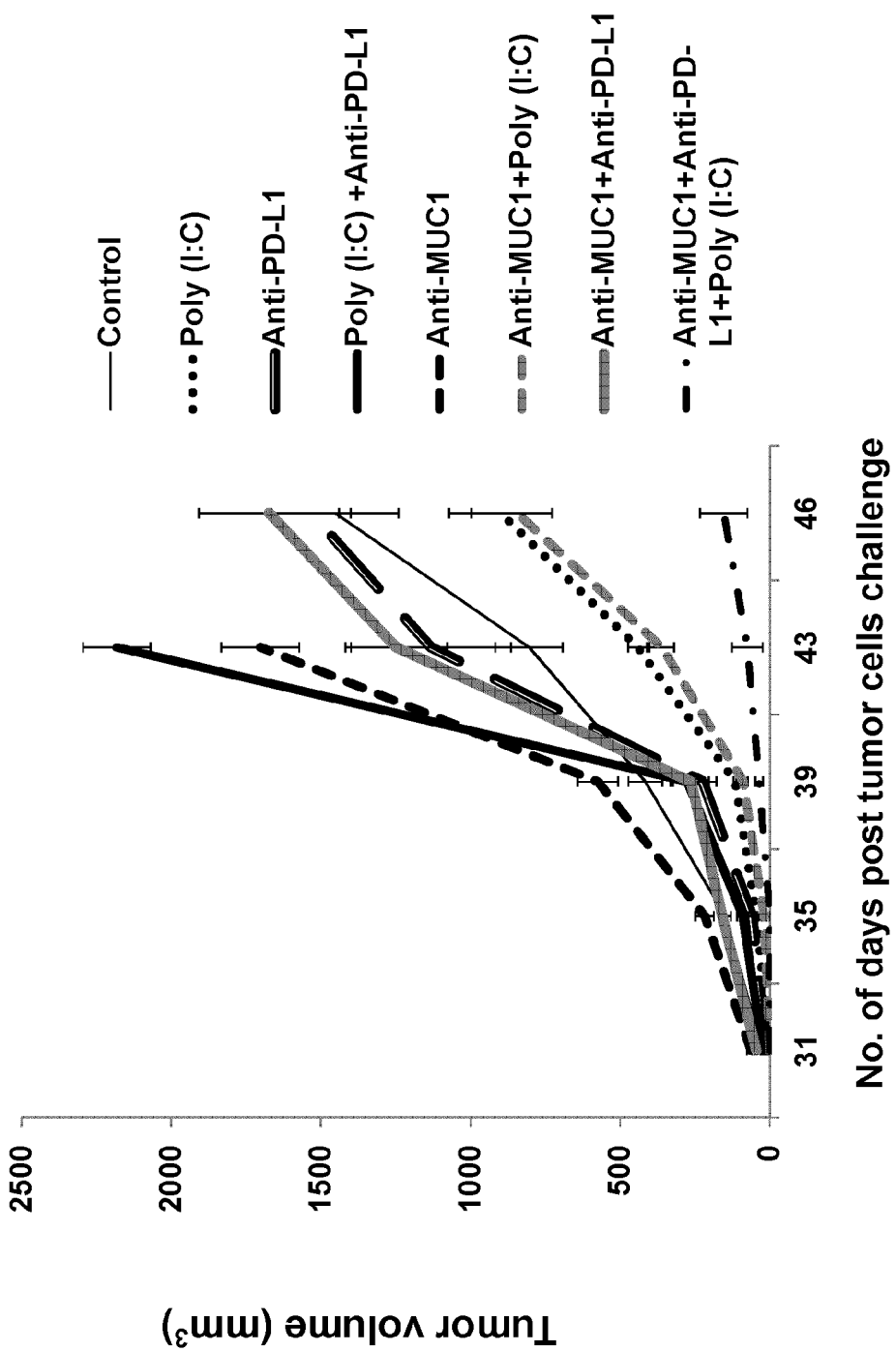
FIG. 11 illustrates the tumor growth curves for different treatment groups post $1^{st}$ challenge with MUC1-Panc02 of tumors over 46 days.

The experimental design is presented in FIG. 9, tumor free survival plotted in FIG. 10 and tumor growth curves by treatment group are plotted in FIG. 11.

The results show in FIG. 10 that the combination treatment with anti-MUC1 IgE, anti-PDL-1, and PolyICLC results in a much reduced tumor growth over the 70+ challenge period (FIG. 10C). None of the animals of the other treatment conditions had a similar tumor growth pattern over the same challenge period (FIGS. 10A-B and D-G), displaying much steeper tumor growth over the same period.

FIG. 11 illustrates that that the combination treatment with anti-MUC1 IgE, anti-PDL-1, and PolyICLC results in much lower tumor volumes over the 46 days challenge period. The tumor volumes in the animals of the other treatment conditions are all larger, with the closest treatment group (anti-MUC1 and anti-PDL-1) having a tumor volume approximately 6.7 time larger than the treatment with anti-MUC1 IgE, anti-PDL-1, and PolyICLC, at the end point of the challenge period.

EXAMPLE 5

Tumor Antigen Specificity

Figure 12:
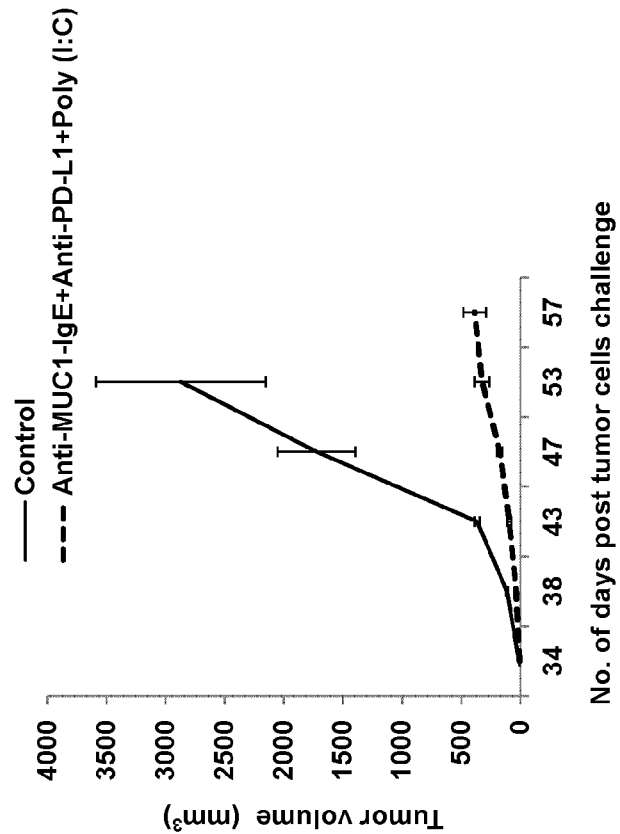
FIG. 12 illustrates the tumor growth curves for MUC1 tumors post re-challenge with MUC1-Panc02 in one flank of surviving mice. A) percent tumor free for anti-MUC1 IgE, anti-PDL-1 and PolyICLC versus control; and B) tumor volume of anti-MUC1 IgE, anti-PDL-1 and PolyICLC versus control, over a 57 day period.
Figure 12:
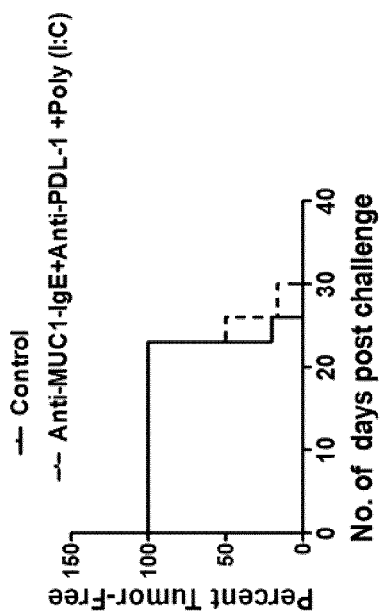
Figure 13:
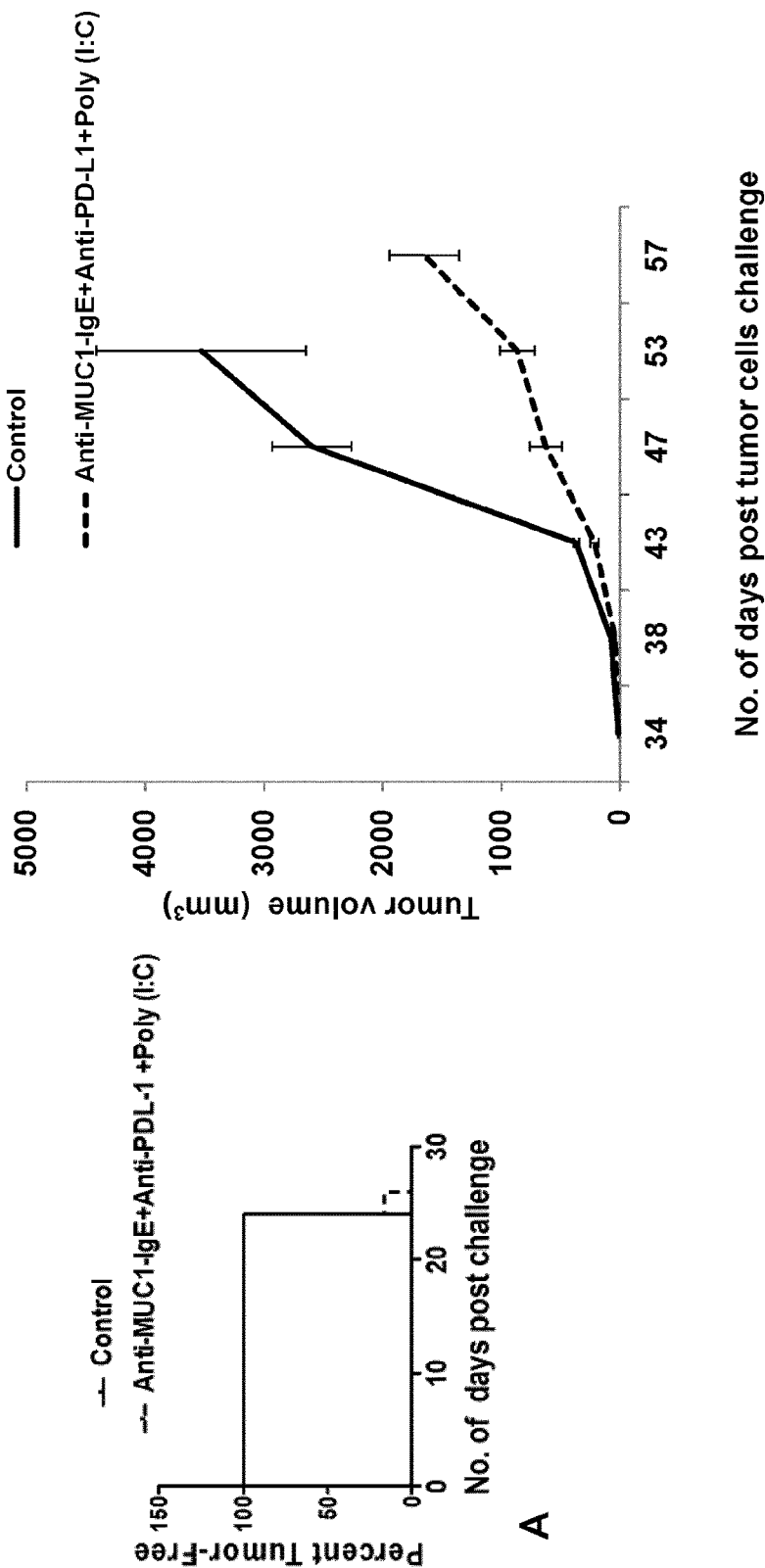
FIG. 13 illustrates the tumor growth curves for Neo tumors post re-challenge with MUC1-Panc02 in the opposite flank of surviving mice. A) percent tumor free for anti-MUC1 IgE, anti-PDL-1 and PolyICLC versus control; and B) tumor volume of anti-MUC1 IgE, anti-PDL-1 and PolyICLC versus control, over a 57 day period.
Figure 14:
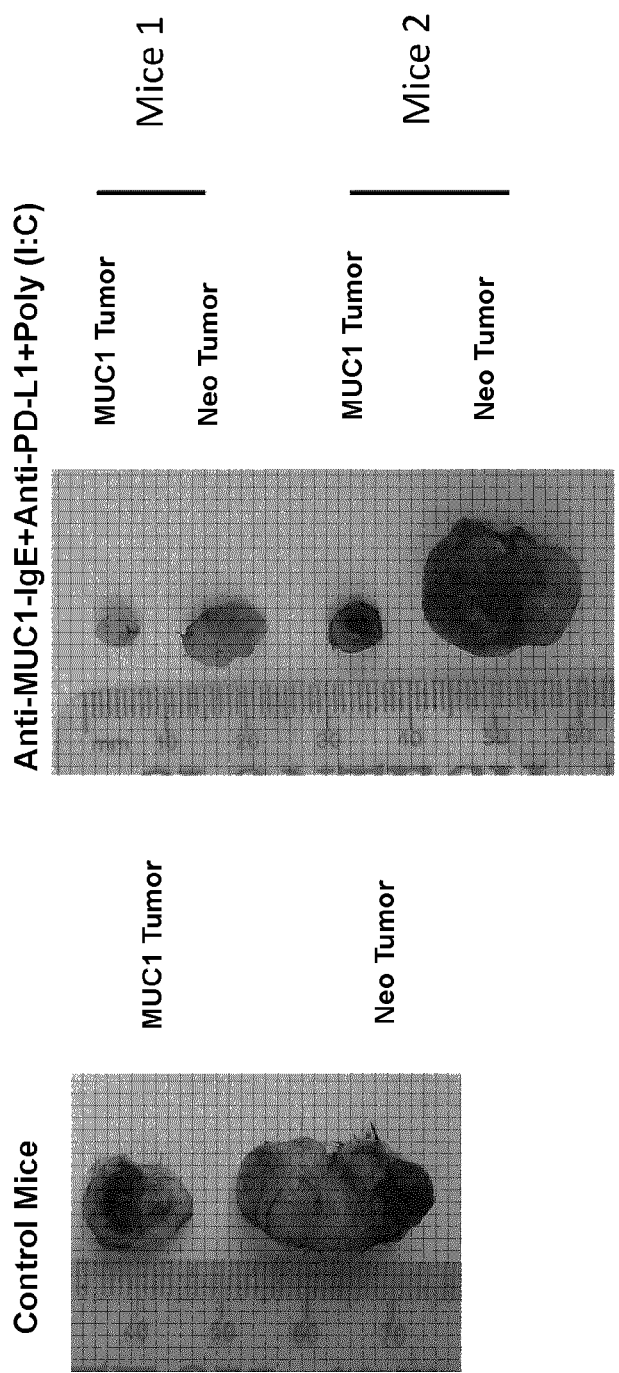
FIG. 14 illustrates images of MUC1 and neo-control tumors from the $2^{nd}$ challenge of combination treatment immunized mice and unimmunized control mice, which confirms the antigen specificity and shows that tumors that do not express MUC1 (Neo Tumor) grow faster than tumor cells that express MUC1 (MUC1 tumor) in mice previously immunized with anti-MUC1IgE and PolyICLC and anti-PDL-1 who had resisted primary tumor challenge.

In order to examine the effect of therapy on T cell memory and specificity in the treated groups, a second round of tumor challenges was performed with $1 \times 10^6$ cells/ml of control (neomycin expressing Panc02-Neo-Panc02) and antigen expressing Panc02 cells-MUC1-Panc02, in mice that previously rejected Pan02.MUC1 tumors. Again, see FIG. 9 for a summary of the experimental protocol. The results of these experiments are found in FIGS. 12-14.

None of the animals rejected the MUC1-Panc02 or the antigen negative control tumor cells (FIGS. 12A and 13A). However, the mice that failed to reject a second round of MUC1-Panc02 cell challenge demonstrated significantly smaller tumors that did not progress as compared to control tumor after 57 days of tumor cell challenge (see FIGS. 12B and 13B, and FIG. 14).

The results of these experiments demonstrate an important interaction between the three immune modulators [anti-MUC1 IgE, anti-PDL-1, and PolyICLC], and demonstrate a potent anti-tumor effect of the combination.

While preferred embodiments have been described above and illustrated in the accompanying drawings, it will be evident to those skilled in the art that modifications may be made without departing from this disclosure. Such modifications are considered as possible variants comprised in the scope of the disclosure.

---

SEQUENCE LISTING

SEQ ID NO: 1
<120> 3C6.hIgE heavy chain variable:
<212> DNA
GCCGCCACCATGTACTTGGGACTGAACTGTGTATTCATAGTTTTTCTCT
TAAATGGTGTCCAGAGTGAAGTGAAGCTTGAGGAGTCTGGAGGAGGCTT
GGTGCAACCTGGAGGATCCATGAAACTCTCTTGTGCTGCCTCTGGATTC
ACTTTTAGTGACGCCTGGATGGACTGGGTCCGCCAGTCTCCAGAGAAGG
GGCTTGAGTGGGTTGCTGAAATTAGAAGCAAAGCTAATAATCATGCAAC
ATACTATGCTGAGTCTGTGAAAGGGAGGTTCACCATCTCAAGAGATGTT
TCCAAAAGTAGTGTCTACCTGCAAATGAACAACTTAAGAGCTGAAGACA
CTGGCATTTATTACTGTACCAGGGGGGGTACGGCTTTGACTACTGGGG
CCAAGGCACCACTCTCACAGTCTCCTCAGGTAAGTG SEQ ID NO: 2
<120> 3C6.hIgE light chain variable:
<212> DNA
GCCGCCACCATGAAGTTGCCTGTTAGGCTGTTGGTGCTGATGTTCTGGA
TTCCTGCTTCCAGCAGTGATGTTTTGATGACCCAAACTCCACTCTCCCT
GCCTGTCAGTCTTGGAGATCAAGCCTCCATCTCTTGCAGATCTAGTCAG
AGCATTGTACATAGTAATGGAAACACCTATTTAGAATGGTACCTGCAGA
AACCAGGCCAGTCTCCAAAGCTCCTGATCTACAAAGTTTCCAACCGATT
TTCTGGGGTCCCAGACAGGTTCAGTGGCAGTGGATCAGGGACAGATTTC
ACACTCAAGATCAGCAGAGTGGAGGCTGAGGATCTGGGAGTTTATTACT

GCTTTCAAGGTTCACATGTTCCGCTCACGTTCGGTGCTGGGACCAAGCT
GGAGCTGAAACGTAAGT

SEQ ID NO: 3
<120> 4H5.hIgE monoclonal antibody heavy chain variable region
<212> DNA
GCCGCCACCATGGGATGGAGCTGTATCATGCTCTTTTTGGTAGCAACAG
CAACAGGTGTCCACTCCCAGGTCCAACTGCAGCAGTCTGGGGCTGAACT
GGTGAAGCCTGGGGCTTCAGTGAAGTTGTCCTGCAAGGCTTCTGGCTAC
ACCTTCACCAGCTACTATATGTACTGGGTGAAGCAGAGGCCTGGACAAG
GCCTTGAGTGGATTGGAGAGATTAATCCTAGCAATGGTGGTACTGACTT
CAATGAGAAGTTCAAGAGCAAGGCCACACTGACTGTAGACAAATCCTCC
AGCACAGCATACATGCAACTCAGCAGCCTGACATCTGCGGACTCTGCGG
TCTATTACTGTACAAGGGGGGGTGATTACCCCTGGTTTGCTTACTGGGG
CCAAGGGACTCTGGTCACTGTCTCTGCAGGTAAGT SEQ ID NO: 4
<120> 4H5.hIgE monoclonal antibody heavy chain variable region
<212> DNA
GCCGCCACCATGGATTCACAGGCCCAGGTTCTTATGTTACTGCTGCTAT
GGGTATCTGGTACCTGTGGGGACATTGTGATGTCACAGTCTCCATCCTC
CCTAGCTGTGTCAGTTGGAGAGAAGGTTACTATGAGCTGCAAGTCCAGT
CAGAGCCTTTTATATAGTAGCAATCAAAAGAACTACTTGGCCTGGTACC
AGCAGAAACCAGGGCAGTCTCCTAAACTGCTGATTTACTGGGCATCCAC
TAGGGAATCTGGGGTCCCTGATCGCTTCACAGGCAGTGGATCTGGGACA
GATTTCACTCTCACCATCAGCAGTGTGAAGGCTGAAGACCTGGCAGTTT
ATTACTGTCAGCAATATTATAGCTATCCTCTCACGTTCGGTGCTGGGAC
CAAGCTGGAGCTGAAACGTAAGT SEQ ID NO: 5
<120> Amino Acid Sequence of MUC1 epitope
<212> Amino Acid
STAPPAHGVTSAPDTRPAPG

---

The invention claimed is:

1. A method for inhibiting growth of a cancer expressing MUC1 on the cancer cell surface in a patient comprising administering to said patient a therapeutic monoclonal antibody specific to MUC1, a TLR3 agonist, and an anti-PD-L1 antibody, wherein:

the therapeutic monoclonal antibody specific to MUC1 is (1) monoclonal antibody AR20.5; or (2) a monoclonal IgE antibody having a heavy chain variable region encoded by SEQ ID NO: 1 and a light chain variable region encoded by SEQ ID NO: 2;

the TLR3 agonist is polyICLC; and the anti-PD-L1 antibody is monoclonal antibody 10F.9G2.

2. The method of claim 1, wherein said therapeutic monoclonal antibody specific to MUC1 is monoclonal antibody 3C6.hIgE.

3. The method of claim 1, wherein said therapeutic monoclonal antibody specific to MUC1 is monoclonal antibody AR20.5 or monoclonal antibody 3C6.hIgE, and said anti-PD-L1 antibody is monoclonal antibody 10F.9G2.

4. The method of claim 1, wherein said therapeutic monoclonal antibody specific to MUC1 is a murine monoclonal antibody or a chimeric monoclonal antibody.

5. The method of claim 4, wherein said therapeutic monoclonal antibody specific to MUC1 has a constant region that is of human origin.

6. The method of claim 1, wherein said cancer is selected from the group consisting of pancreatic cancer, breast cancer, colorectal cancer, ovarian cancer, renal cancer, prostate cancer, bladder cancer, gastrointestinal cancer, lung cancer and multiple myeloma.

7. The method of claim 1, comprising the steps of:
a) administering a therapeutically effective amount of said therapeutic monoclonal antibody specific to MUC 1;
b) administering a therapeutically effective amount of said TLR3 agonist after step a); and
c) administering a therapeutically effective amount of said anti-PD-L1 antibody, after step b).

8. The method of claim 7, wherein step b) is performed 1 or more days after step a).

9. The method of claim 7, wherein step c) is performed 1 or more days after step b).

* * * * *